United States Patent [19]

Saikawa et al.

[11] 4,317,907
[45] * Mar. 2, 1982

[54] PROCESS FOR PRODUCING 7-(SUBSTITUTED)AMINO-3-SUBSTITUTED THIOMETHYL CEPHEM CARBOXYLIC ACIDS

[75] Inventors: Isamu Saikawa; Shuntaro Takano, both of Toyama; Kaishu Momonoi, Shinminato; Isamu Takakura, Toyama; Seietsu Kuroda, Toyama; Kiyoshi Tanaka, Toyama; Kenshin Hayashi, Tonami; Bunei Nagahashi, Toyama; Chiaki Kutani, Funabashi, all of Japan

[73] Assignee: Toyama Chemical Co., Ltd., Tokyo, Japan

[*] Notice: The portion of the term of this patent subsequent to Jan. 26, 1999, has been disclaimed.

[21] Appl. No.: 874,637

[22] Filed: Feb. 2, 1978

[30] Foreign Application Priority Data

Feb. 8, 1977 [JP] Japan .................................. 52-12182
Nov. 24, 1977 [JP] Japan ................................ 52-139840

[51] Int. Cl.$^3$ ............................................. C07D 501/04
[52] U.S. Cl. ...................................... 544/21; 542/420; 544/26; 544/27
[58] Field of Search ...................... 544/26, 27, 28, 21, 544/30, 16; 542/420

[56] References Cited

U.S. PATENT DOCUMENTS

| | | | |
|---|---|---|---|
| 3,261,832 | 7/1966 | Cowley et al. | 544/27 |
| 3,516,997 | 6/1970 | Takano et al. | 260/243 C |
| 3,833,572 | 9/1974 | Clark et al. | 544/17 |
| 3,840,531 | 10/1974 | Greene | 260/243 C |
| 3,872,115 | 3/1975 | Sugimoto et al. | 544/27 |
| 4,014,874 | 3/1977 | Peter et al. | 260/243 C |
| 4,144,391 | 3/1979 | Hatfield | 544/27 |

FOREIGN PATENT DOCUMENTS

| | | |
|---|---|---|
| 650444 | 11/1965 | Belgium . |
| 650445 | 11/1965 | Belgium . |
| 1795484 | 5/1962 | Fed. Rep. of Germany . |
| 2065621 | 4/1970 | Fed. Rep. of Germany . |
| 2332045 | 6/1973 | Fed. Rep. of Germany . |
| 2530622 | 7/1975 | Fed. Rep. of Germany . |
| 2537974 | 8/1975 | Fed. Rep. of Germany . |
| 1400804 | 7/1975 | United Kingdom ................ 260/243 |

OTHER PUBLICATIONS

Cocker et al., J. Chem. Soc., pp. 5015–5031 (1965).
Taylor, J. Chem. Soc., pp. 7020–7029 (1965).
Central Patents Index Week U28, Aug. 16, 1973.
Central Patents Index Week U48, Jan. 3, 1974.
Central Patents Index Week V3, Feb. 21, 1974.
Central Patents Index Week V12, Apr. 30, 1974.
Central Patents Index Week V25, Jul. 30, 1974.
Central Patents Index Week V38, Oct. 29, 1974.
Central Patents Index Week V39, Nov. 5, 1974.
Central Patents Index Week V49, Jan. 14, 1975.
Central Patent Index Week W7, Mar. 25, 1979.
Central Patent Index Week X6, Mar. 16, 1976.
Central Patent Index Week X40, Nov. 10, 1976.
CA, vol. 85, 1976 46749j.
Breslow et al., JACS, vol. 62, 2385–2388 (1960).
Wenkert et al., JACS, vol. 78, 2318–2325 (1956).
Karady et al., Tetrahedron Letters No. 30, 2625–2628 (1974).

*Primary Examiner*—Nicholas S. Rizzo
*Attorney, Agent, or Firm*—Oblon, Fisher, Spivak, McClelland & Maier

[57] ABSTRACT

This disclosure relates to a novel process for producing 7-(substituted)amino-3-substituted thiomethyl cephem carboxylic acids which are intermediate products of cephalosporins being valuable antibacterial compounds for use in mammals including man.

88 Claims, No Drawings

PROCESS FOR PRODUCING 7-(SUBSTITUTED)AMINO-3-SUBSTITUTED THIOMETHYL CEPHEM CARBOXYLIC ACIDS

This invention relates to a novel process for producing 7-(substituted)amino-3-substituted thiomethyl cephem carboxylic acids.

Many publications, for example, German Offenlegungsschrift Nos. 1,795,484; 2,018,600; and 2,065,621, U.S.P. 3,516,997, and Japanese Patent Application Kokai (Laid-Open) No. 154,287/75, report reacting a thiol compound or its salt with the acetoxy group in the 3-position of a 7-aminocephalosporanic acid or a derivative in the carboxyl group thereof or a salt thereof to convert the acetoxy group in the 3-position. Said publications disclose that it is not desirable to effect said reaction in an organic solvent free from water and it is preferable to effect the reaction in water or an aqueous organic solvent at a pH of 6 to 7. However, even under said preferable reaction conditions, the product obtained is extremely impure and the yield is 30 to 50%. The present inventors' duplication of said reaction has clarified that the yield is 30 to 50% at most and the product is in admixture with the starting 7-aminocephalosporanic acid. On the other hand, U.S. Pat. No. 3,840,531; Japanese Patent Application Kokai (Laid-Open) Nos. 295/74 and 10,077/73, German Offenlegungsschrift No. 2,332,045, Japanese Patent Publication No. 13,023/71 and the like report a method for smoothly carrying out the conversion in the 3-position by which a 7-aminocephalosporanic acid or its salt, the amino group in the 7-position of which has been protected with an acyl group, such as formyl, lower alkanoyl or the like, or cephalosporin C or a derivative thereof is used as the starting material. However, said publications describe that even according to said method, it is preferable to carry out the reaction in water or an aqueous organic solvent in the vicinity of neutral.

Concerning a method by which a cephalosporin C derivative is used as the starting material, it is reported in, for example, British Pat. No. 1,400,804, and Japanese Patent Application Kokai (Laid-Open) No. 95,088/76, that the conversion in the 3-position is effected in water or an aqueous organic solvent in the presence of a halide or inorganic salt of a metal of Group I or II of the Periodic Table, such as KI, NaI-CaI$_2$, BaI$_2$, NaCl, NH$_4$Cl, BaCl$_2$, MgCl$_2$ or the like. However, the methods by which an acylated cephalosporanic acid, cephalosporin C or its derivative is used as the starting material is complicated in reaction because the amino group in the 7-position must be acylated, or an acylated starting material must be used and the acyl group must be removed by iminohalogenation, iminoetherification, hydrolysis or the like after the conversion in the 3-position. In said reaction, the conversion per se in the 3-position with a thiol or its salt is effected in an aqueous solvent under the above-mentioned preferable conditions, and in general, the yield is 60 to 80%.

On the above-mentioned background, the present inventors have conducted extensive research with an intention of developing a method for converting the group in the 3-position with a thiol compound or its salt in a high yield with ease in industry, and consequently, have unexpectedly found that when the reaction is effected in a non-aqueous solvent in the presence of boron trifluoride or its complex compound a satisfactory result is obtained.

An object of this invention is to provide a process for producing a 7-(substituted)amino-3-substituted thiomethyl cephem carboxylic acid or a derivative in the carboxyl group thereof or a salt thereof which is important as an intermediate of a cephalosporin compound from a cephalosporanic acid or a derivative in the carboxyl group thereof in a high yield and a high purity by means of an industrially easy operation.

Other objects and advantages of this invention will be apparent from the following description.

According to this invention, there is provided a process for producing a 7-(substituted)-amino-3-substituted thiomethyl cephem carboxylic acid represented by the general formula (I)

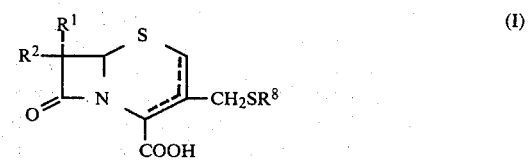

wherein $R^1$ is a hydrogen atom or a $C_{1-4}$ alkyloxy group; $R^2$ is an amino group or a group represented by the formula,

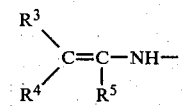

in which $R^3$, $R^4$, and $R^5$, which may be identical or different, are hydrogen or organic residues which do not participate in the reaction, or the formula,

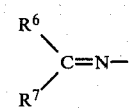

in which $R^6$ and $R^7$, which may be identical or different, are hydrogen or organic residues which do not participate in the reaction; $R^8$ is a thiol compound residue; and the dotted line in the cephem ring means that there is a double bond between the 3- and 4-positions or between the 2- and 3-positions, a derivative in the carboxyl group of the above carboxylic acid or a salt thereof, which comprises reacting a cephalosporanic acid represented by the general formula (II),

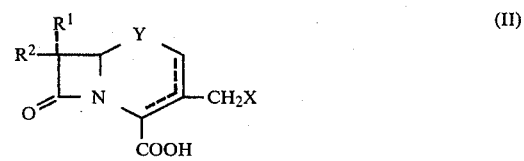

wherein $R^1$ and $R^2$ are the same as defined above; X is an unsubstituted or substituted acyloxy or carbamoyloxy group; >Y is >S or >S→O, and the dotted line in the cephem ring has the same meaning as defined above, or a derivative in the carboxyl group of said cephalosporanic acid, or a salt thereof, with a thiol compound represented by the general formula (III), $$R^8-SH \quad (III)$$

wherein $R^8$ has the same meaning as defined above, or a salt of the thiol compound, in an organic solvent in the presence of boron trifluoride or its complex compound. According to said process, a good result is obtained in the case of not only $\Delta^3$-cephem compound but also $\Delta^2$-cephem compound, and there can be used not only a compound having $>Y$ being $>S$ but also a chemically stable compound having $>Y$ being $>S\rightarrow O$ as the starting material. In the latter case, reduction reaction of $>S\rightarrow O$ takes place owing to the presence of boron trifluoride of its complex compound, thereby obtaining a compound having $>Y$ being $>S$.

As the $C_{1-4}$ alkyloxy group for $R^1$ in the general formulas (I) and (II) mentioned above, there may be exemplified methoxy, ethoxy, propoxy, butoxy and the like.

As the unsubstituted or substituted acyloxy or carbamoyloxy group for X in the general formula (II), there may be exemplified $C_{1-8}$ alkanoyloxy groups, for example, formyloxy, acetoxy, propionyloxy, butyryloxy and the like; $C_{3-8}$ alkenoyloxy groups, for example, acryloyloxy and the like; $C_{7-11}$ aroyloxy groups, for example, benzoyloxy, naphthoyloxy, and the like; $C_{8-9}$ aralkanoyloxy groups, for example, phenylacetoxy, phenylpropionyloxy and the like; carbamoyloxy groups; and the like, of which $C_{1-8}$ acyloxy groups and carbamoyloxy groups are preferable. As the substituent of the substituted acyloxy or carbamoyloxy group, there may be exemplified known substituents for acyloxy and carbamoyloxy groups, such as halogen, nitro, $C_{1-4}$ alkyl, $C_{1-4}$ alkoxy, $C_{1-4}$ alkylthio, $C_{1-8}$ acyloxy, $C_{1-8}$ acylamino, hydroxyl, carboxyl, sulfamoyl, carbamoyl, cyano, carboxy-$C_{1-4}$ alkoxycarbamoyloxy, benzoylcarbamoyl, carboxy-$C_{1-4}$ alkoxysulfamoyl, and the like.

In the general formulas (I) and (II), $R^2$ is an amino group or a group represented by the formula

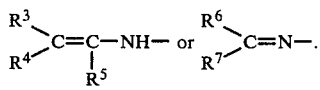

The formula

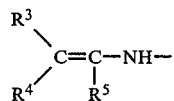

may also be rewritten

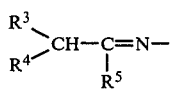

as an isomer, and the latter is also included in this invention.

As the organic residues for $R^3$, $R^4$, $R^5$, $R^6$ and $R^7$ which do not participate in the reaction, there may be used those known in this field, and examples thereof are unsubstituted or substituted aliphatic residues, alicyclic residues, aromatic residues, araliphatic residues, heterocyclic residues, acyl groups and the like. More specifically, the following groups may be exemplified:

(1) Aliphatic residue: alkyl groups, for instance, methyl, ethyl, propyl, butyl, isobutyl, pentyl and the like; and alkenyl groups, for instance, vinyl, propenyl, butenyl and the like.

(2) Alicyclic residue: cycloalkyl groups, for instance, cyclopentyl, cyclohexyl, cycloheptyl and the like; and cycloalkenyl groups, for instance, cyclopentenyl, cyclohexenyl and the like.

(3) Aromatic residue: aryl groups, for instance, phenyl, naphthyl and the like.

(4) Araliphatic residue: aralkyl groups, for instance, benzyl, phenethyl and the like.

(5) Heterocyclic residue: heterocyclic groups containing one or more hetero atoms (oxygen, nitrogen and sulfur) in any combination in any position in the molecule, for instance, pyrrolidyl, piperazinyl, furyl, thienyl, pyrrolyl, pyrazolyl, oxazolyl, thiazolyl, pyridyl, imidazolyl, quinolyl, benzothiazolyl, oxadiazolyl, thiadiazolyl, triazolyl, tetrazolyl and the like.

(6) Acyl group: acyl groups derived from organic carboxylic acids. As said organic carboxylic acids, there may be exemplified aliphatic carboxylic acids; alicyclic carboxylic acids; alicycloaliphatic carboxylic acids; araliphatic carboxylic acids, aromatic oxy aliphatic carboxylic acids, aromatic thio aliphatic carboxylic acids, heterocyclic ring-substituted aliphatic carboxylic acids, heterocyclic oxy aliphatic carboxylic acids, and heterocyclic thio aliphatic carboxylic acids, in which an aromatic residue or heterocyclic group is bonded to an aliphatic carboxylic acid directly or through an oxygen or sulfur atom; organic carboxylic acids in which an aromatic ring, an aliphatic group or an alicyclic group is bonded to the carbonyl group through an oxygen, nitrogen or sulfur atom; aromatic carboxylic acids; and heterocyclic carboxylic acids.

As the above aliphatic carboxylic acids, there may be exemplified formic acid, acetic acid, propionic acid, butanoic acid, isobutanoic acid, pentanoic acid, methoxyacetic acid, methylthioacetic acid, acrylic acid, crotonic acid and the like. As the above alicyclic carboxylic acids, there may be exemplified cyclohexanoic acid and the like, and as the above alicycloaliphatic carboxylic acids, there may be exemplified cyclopentane-acetic acid, cyclohexane-acetic acid, cyclohexane-propionic acid, cyclohexadiene-acetic acid and the like. As the aromatic residue in the above organic carboxylic acids, there may be exemplified phenyl, naphthyl, and the like, and as the heterocyclic residue, there may be exemplified residues of heterocyclic compounds containing at least one hetero atom in the ring, such as furane, thiophene, pyrrole, pyrazole, imidazole, triazole, thiazole, isothiazole, oxazole, isoxazole, thiadiazole, oxadiazole, thiatriazole, oxatriazole, tetrazole, benzoxazole, benzofuran and the like.

Each of the groups constituting the above organic carboxylic acid may be further substituted by a substituent, for example, a halogen atom, a hydroxyl group, a protected hydroxyl group, a $C_{1-5}$alkyl group, a $C_{1-5}$alkoxy group, a $C_{1-4}$acyl group, a nitro group, an amino group, a protected amino group, a mercapto group, a protected mercapto group, a carboxyl group, a protected carboxyl group or the like.

As the protecting groups in the above-mentioned protected hydroxyl, protected amino, protected mercapto and protected carboxyl groups, there may be used those which will be mentioned hereinafter concerning substituents in the $R^8$ group.

$R^3$, $R^4$ and $R^5$ may be identical or different, and are preferably hydrogen, $C_{1-5}$alkyl, $C_{2-4}$alkenyl, $C_{5-7}$cycloalkyl, $C_{5-7}$cycloalkenyl, aryl, aralkyl, heterocyclic containing O, N and S alone or in any combination in any position, or acyl, and $R^6$ and $R^7$ may be identical or different, and are preferably hydrogen, $C_{1-5}$alkyl, $C_{2-4}$alkenyl, $C_{5-7}$cycloalkyl, $C_{5-7}$cycloalkenyl, aryl, aralkyl, heterocyclic containing O, N, and S alone or in any combination in any position, or acyl.

As the derivatives in the carboxyl group of the compounds represented by the general formulas (I) and (II), there may be exemplified derivatives known usually in the field of penicillin and cephalosporin, for example, the following compounds:

(a) Esters: all esters which do not affect the reaction at all are included, for example, substituted or unsubstituted alkyl esters, such as methyl ester, ethyl ester, propyl ester, isopropyl ester, butyl ester, tert.-butyl ester, methoxymethyl ester, ethoxymethyl ester, phenoxymethyl ester, methylthiomethyl ester, methylthioethyl ester, phenylthiomethyl ester, dimethylaminoethyl ester, diethylaminoethyl ester, morpholinoethyl ester, piperidinoethyl ester, acetylmethyl ester, phenacyl ester, toluoylmethyl ester, 4-nitrophenacyl ester, acetoxymethyl ester, pivaloyloxymethyl ester, benzoyloxymethyl ester, 1,1-diacetylmethyl ester, 1-acetyl-1-methoxycarbonylmethyl ester, methanesulfonylethyl ester, toluenesulfonylethyl ester, bromomethyl ester, iodoethyl ester, trichloroethyl ester, cyanomethyl ester, thenoylmethyl ester, phthalimidomethyl ester and the like; cycloalkyl esters, such as cyclohexyl ester, cycloheptyl ester and the like; alkenyl esters, such as propenyl ester, allyl ester, 3-butenyl ester and the like; alkinyl esters, such as propinyl ester and the like; substituted or unsubstituted aryl esters, such as phenyl ester, tolyl ester, xylyl ester, naphthyl ester, p-nitrophenyl ester, 2,4-dinitrophenyl ester, p-methoxyphenyl ester, trichlorophenyl ester, pentachlorophenyl ester, p-methanesulfonylphenyl ester and the like; substituted or unsubstituted aralkyl esters, such as benzyl ester, phenethyl ester, p-chlorobenzyl ester, p-nitrobenzyl ester, p-methoxybenzyl ester, 3,5-dimethoxybenzyl ester, diphenylmethyl ester, bis(4-methoxyphenyl)-methyl ester, 3,5-di-tert.-butyl-4-hydroxybenzyl ester, trityl ester and the like; indanyl ester; phthalidyl ester; other esters formed from a carboxylic acid and thioalcohol, tetrahydrofuranol, 1-cyclopropyle-thanol, 1-phenyl-3-methyl-5-pyrazolone, 3-hydroxypyridine, 2-hydroxypyridine-1-oxide or the like, which may be optionally substituted by a halogen atom, a nitro group, an alkoxy group or the like; and esters formed by reaction between a carboxylic acid and methoxyacetylene, ethoxyacetylene, tert.-butylethinyldimethylamine, ethylethinyldiethylamine, or N-ethyl-5-phenylisoxazolinium-3-sulfonic acid salt.

(b) Anhydrides of the carboxyl group with N-hydroxysuccinic acid imide, N-hydroxyphthalic acid imide, dimethylhydroxylamine, diethylhydroxylamine, 1-hydroxypiperidine, oxime or the like.

(c) Amides: all of acid amides, N-substituted acid amides, and N,N-di-substituted acid amides are included, for example, N-alkyl acid amides, such as N-methyl acid amide, N-ethyl acid amide and the like; N-aryl acid amides, such as N-phenyl acid amide and the like; N,N-dialkyl acid amides, such as N,N-dimethyl acid amide, N,N-diethyl acid amide, N-ethyl-N-methyl acid amide and the like; and acid amides with imidazole, 4-substituted imidazole, triazolopyridone and the like.

The salt in the term "a compound of the general formula (I) or (II), or a derivative in the carboxyl group thereof or a salt thereof" used in the specification and claims means to include both salt at the acidic group (for example, carboxyl group) and salt at the basic group (for example, amino group). As the salt at the acidic group, there may be exemplified salts with alkali metals such as sodium, potassium and the like; salts with alkaline earth metals such as calcium, magnesium and the like; ammonium salts; salts with nitrogen-containing organic bases such as triethylamine, diethylamine, pyridine, N-methylpiperidine, N-methylmorpholine, N,N-dimethylaniline and the like. As the salt at the basic group, there may be exemplified salts with mineral acids, such as hydrochloric acid, sulfuric acid and the like; salts with organic acids such as oxalic acid, formic acid, trichloroacetic acid, trifluoroacetic acid and the like; and salts with sulfonic acids, such as methanesulfonic acid, toluenesulfonic acid, naphthalenesulfonic acid and the like. These salts may be previously prepared and isolated or may be prepared in the reaction system. Hydrates of the starting and objective compounds mentioned above are also included in this invention.

$R^8$ in the general formulas (I) and (III) represents residues of thiol compounds known in the field of cephalosporin, and includes, for example, unsubstituted or substituted alkyl, cycloalkyl, aryl, aralkyl, acyl, thiocarbamoyl, alkoxythiocarbonyl, aryloxythiocarbonyl, cycloalkyloxythiocarbonyl, amidino, and heterocyclic groups. More specifically, there may be exemplified $C_{1-8}$alkyl, such as methyl, ethyl, propyl, butyl, isobutyl and the like; $C_{5-7}$-cycloalkyl, such as cyclohexyl, cycloheptyl and the like; $C_{7-9}$aralkyl, such as benzyl, phenethyl, and the like; aryl, such as phenyl, naphthyl and the like; acyl, such as acetyl, propionyl, butyryl, benzoyl, naphthoyl, cyclopetanecarbonyl, cyclohexanecarbonyl, furoyl, thenoyl, isothiazolecarbonyl, isoxazolecarbonyl, thiadiazolecarbonyl, triazolecarbonyl and the like; thiocarbamoyl, such as thiocarbamoyl, N-methylthiocarbamoyl, N,N-diethylthiocarbamoyl, 1-piperidinothiocarbonyl, 1-morpholinothiocarbonyl, 4-methyl-1-piperazinylthiocarbonyl, and the like; $C_{1-4}$alkoxythiocarbonyl, such as methoxythiocarbonyl, ethoxythiocarbonyl, propoxythiocarbonyl, butoxythiocarbonyl and the like; aryloxythiocarbonyl, such as phenoxythiocarbonyl and the like; $C_{5-7}$cycloalkyloxythiocarbonyl, such as cyclohexyloxythiocarbonyl and the like; amidino, such as amidino, N-methylamidino, N,N'-dimethylamidino, and the like; and heterocyclic groups, such as oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, oxadiazolyl, thiadiazolyl, triazolyl, thiatriazolyl, tetrazolyl, triazinyl, benzimidazolyl, benzoxazolyl, benzothiazolyl, triazolopyridyl, purinyl, pyridine-1-oxide-2-yl, pyridazine-1-oxide-6-yl, tetrazolopyridazinyl, tetrazolopyrimidinyl, thiazolopyridazinyl, thiadiazolopyridazinyl, triazolopyridazinyl, and the like. As the heterocyclic group for $R^8$, nitrogen-containing heterocyclic groups which contain at least one nitrogen atom with or without oxygen or sulfur atom are preferable.

Furthermore, the groups for R⁸ may be substituted by at least one substituent, such as halogen, $C_{1-4}$alkyl, phenyl, hydroxyl, mercapto, $C_{1-4}$alkoxy, $C_{1-4}$alkylthio, nitro, cyano, cyano-$C_{1-4}$alkyl, amino, $C_{1-4}$alkylamino, di-$C_{1-4}$alkylamino, $C_{1-8}$acylamino, $C_{1-8}$acyl, $C_{1-8}$acyloxy, carboxyl, carbamoyl, amino-$C_{1-4}$alkyl, N-$C_{1-4}$alkylamino-$C_{1-4}$alkyl, N,N-di-$C_{1-4}$-alkylamino-$C_{1-4}$alkyl, hydroxy-$C_{1-4}$alkyl, $C_{1-4}$alkoxy-$C_{1-4}$alkyl, carboxy-$C_{1-4}$alkyl, sulfo-$C_{1-4}$alkyl, sulfo, sulfamoyl-$C_{1-4}$alkyl, sulfamoyl, carbamoyl-$C_{1-4}$alkyl, $C_{2-4}$alkenyl, carbamoyl-$C_{2-4}$alkenyl, N-$C_{1-4}$alkylcarbamoyl, N,N-di-$C_{1-4}$alkylcarbamoyl, $C_{1-8}$acyl-$C_{1-4}$alkyl, N-$C_{1-4}$alkylcarbamoyl-$C_{1-4}$alkyl, N,N-di-$C_{1-4}$-alkylcarbamoyl-$C_{1-4}$alkyl, and the like, and among these substituents, the hydroxyl, mercapto, amino and carboxyl groups may be protected with an appropriate protecting group which is usually used in the field of penicillin or cephalosporin. The protecting group for the amino group includes all groups which can be used as common amino-protecting groups, for example, trichloroethoxycarbonyl, tribromoethoxycarbonyl, benzyloxycarbonyl, p-toluenesulfonyl, p-nitrobenzyloxycarbonyl, o-bromobenzyloxycarbonyl, o-nitrophenylsulfenyl, chloroacetyl, trifluoroacetyl, formyl, tert.-butoxycarbonyl, p-methoxybenzyloxycarbonyl, 3,4-dimethoxybenzyloxycarbonyl, 4-(phenylazo)benzyloxycarbonyl, 4-(4-methoxyphenylazo)benzyloxycarbonyl, pyridine-1-oxide-2-yl-methoxycarbonyl, 2-pyridylmethoxycarbonyl, 2-furyloxycarbonyl, diphenylmethoxycarbonyl, 1,1-dimethylpropoxycarbonyl, isopropoxycarbonyl, 1-cyclopropylethoxycarbonyl, phthaloyl, succinyl, 1-adamantyloxycarbonyl, 8-quinolyloxycarbonyl and the like, which are easily removable acyl groups; other easily removable groups such as trityl, 2-nitrophenylthio, 2,4-dinitrophenylthio, 2-hydroxybenzylidene, 2-hydroxy-5-chlorobenzylidene, 2-hydroxy-1-naphthylmethylene, 3-hydroxy-4-pyridylmethylene, 1-methoxycarbonyl-2-propylidene, 1-ethoxycarbonyl-2-propylidene, 3-ethoxycarbonyl-2-butylidene, 1-acetyl-2-propylidene, 1-benzoyl-2-propylidene, 1-[N-(2-methoxyphenyl)carbamoyl]-2-propylidene, 1-[N-(4-methoxyphenyl)carbamoyl]-2-propylidene, 2-ethoxycarbonylcyclohexylidene, 2-ethoxycarbonylcyclopentylidene, 2-acetylcyclohexylidene, 3,3-dimethyl-5-oxycyclohexylidene and the like; and di- or tri-alkylsilyl.

The protecting groups for the hydroxyl and mercapto groups include all groups that can usually be used as protecting groups for hydroxyl and mercapto groups, for example, easily removable acyl groups such as benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, 4-(phenylazo)-benzyloxycarbonyl, 4-(4-methoxyphenylazo)benzyloxycarbonyl, tert.-butoxycarbonyl, 1,1-dimethylpropoxycarbonyl, isopropoxycarbonyl, diphenylmethoxycarbonyl, 2-pyridylmethoxycarbonyl, 2,2,2-trichloroethoxycarbonyl, 2,2,2-tribromoethoxycarbonyl, 2-furfuryloxycarbonyl, 1-adamantyloxycarbonyl, 1-cyclopropylethoxycarbonyl, 3-quinolyloxycarbonyl, trifluoroacetyl and the like; benzyl; trityl; methoxymethyl; 2-nitrophenylthio; 2,4-dinitrophenylthio and the like.

The protecting group for the carboxyl group include all groups that can usually be used as carboxyl-protecting groups, for example, ester-forming groups, such as methyl, ethyl, propyl, isopropyl, tert.-butyl, butyl, benzyl, diphenylmethyl, triphenylmethyl, p-nitrobenzyl, p-methoxybenzyl, benzoylmethyl, acetylmethyl, p-nitrobenzoylmethyl, p-bromobenzoylmethyl, p-methanesulfonylbenzoylmethyl, phthalimidomethyl, trichloroethyl, 1,1-dimethyl-2-propinyl, acetoxymethyl, propionyloxymethyl, pivaloyloxymethyl, 1,1-dimethylpropyl, 1,1-dimethyl-2-propenyl, 3-methyl-3-butenyl, succinimidomethyl, 1-cyclopropylethyl, metylsulfenylmethyl, phenylsulfenylmethyl, methylthiomethyl, phenylthiomethyl, dimethylaminomethyl, quinoline-1-oxide-2-yl-methyl, pyridine-1-oxide-2-yl-methyl, di-(p-methoxyphenyl)methyl and the like; silyl residues of silyl compounds disclosed in Japanese Patent Application Kokai (Laid-Open) No. 7073/71 and Dutch Patent Application No. 7105259 (already laid open to the public inspection), such as dimethyldichlorosilane; non-metallic residues of non-metalic compounds disclosed in German Offenlegungsschrift No. 2,062,925, such as titanium tetrachloride; and the like.

Salts of the thiol compound represented by the general formula (III) may be in the basic salt form or in the acidic salt form depending upon the type of R⁸ and include both the basic and acidic salts. As to examples of the salt, the explanation of the salt of the compounds represented by the general formulas (I) and (II) mentioned above applies. As the material for forming the salt of the thiol compound, there may be used the materials for forming the salts of the compounds represented by the general formulas (I) and (II).

As the complex compound of boron trifluoride, there may be exemplified complex salts with dialkyl ether, such as diethyl ether, di-n-propyl ether, di-n-butyl ether and the like; complex salts with amines, such as ethylamine, n-propylamine, isopropylamine, n-butylamine, triethanolamine and the like; complex salts with aliphatic acids, such as acetic acid, propionic acid and the like; complex salts with nitriles, such as acetonitrile, propionitrile, and the like; complex salts with carboxylic esters, such as methyl formate, ethyl formate, ethyl acetate and the like; and complex salts with phenols, such as phenol and the like; and the like, among which the dialkyl ether complex salts, aliphatic acid complex salts and nitrile complex salts are particularly preferred. These complex compounds of boron trifluoride are commonly characterized as coordination compounds of boron trifluoride.

The compound represented by the general formula (II) in which R² is

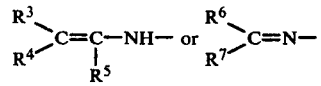

in which R³, R⁴, R⁵, R⁶ and R⁷ are the same as defined above can be synthesized by reacting 7-aminocephalosporanic acid with an aldehyde or a ketone in an inert solvent (Japanese Patent Publication No. 28,913/69), and the compound represented by the general formula (II) wherein R¹ is a $C_{1-4}$alkyloxy group can be synthesized by introducing the $C_{1-4}$alkyloxy group into the compound represented by the general formula (II) in which R¹ is a hydrogen atom in a manner known per se (Journal of Synthetic Organic Chemistry, Japan, 35, 563–574 (1977), etc.).

As the organic solvent used in the process of this invention, there may be used all organic solvents which do not adversely affect the reaction, and preferable are nitriles, nitroalkanes, organic carboxylic acids, ketones, ethers and sulfolanes. These solvents may be used in admixture of two or more. The above nitriles include, for example, aliphatic nitriles, aliphatic dinitriles, aromatic nitriles, and heterocyclic nitriles, such as acetonitrile, propionitrile, butyronitrile, isobutyronitrile, valeronitrile, isovaleronitrile, capronitrile, enanthonitrile, caprylonitrile, pelargononitrile, caprinitrile, crotononitrile, lauronitrile, palmitonitrile, stearonitrile, acrylonitrile, malononitrile, succinonitrile, glutaronitrile, adiponitrile, benzonitrile, tolunitrile, cyanated benzyl, cinnamonitrile, naphthonitrile, cyanothiophene, and the like. The nitroalkanes include nitromethane, nitroethane, nitropropane, nitrobutane, nitropentane, nitrohexane, nitroheptane, nitrooctane and the like. The organic carboxylic acids include aliphatic saturated monocarboxylic acids and aliphatic saturated dicarboxylic acids, such as formic acid, acetic acid, propionic acid, lactic acid, isolatic acid, valeric acid, isovaleric acid, pivalic acid, trifluoroacetic acid and the like. The ketones include aliphatic saturated ketones, aliphatic unsaturated ketones, alicyclic ketones, aromatic ketones, and heterocyclic ketons, such as acetone, ethyl methyl ketone, methyl propyl ketone, isopropyl methyl ketone, butyl methyl ketone, isobutyl methyl ketone, diethyl ketone, diisopropyl ketone, mesityl oxide, methylheptenone, cyclobutanone, cyclopentanone, cyclohexanone, acetophenone, propiophenone, butyrophenone, valerophenone, dibenzyl ketone, acetothienone, 2-acetofurone, and the like. The ethers include aliphatic saturated ethers, aliphatic unsaturated ethers, aromatic ethers, and cyclic ethers such as diethyl ether, dipropyl ether, diisopropyl ether, dibutyl ether, diisobutyl ether, methyl ethyl ether, methyl propyl ether, methyl isopropyl ether, methyl butyl ether, methyl isobutyl ether, ethyl propyl ether, ethyl isopropyl ether, ethyl butyl ether, ethyl isobutyl ether, ethylene glycol dimethyl ether, diallyl ether, methyl allyl ether, ethyl allyl ether, anisole, phenetole, dibenzyl ether, phenyl benzyl ether, tetrahydrofuran, tetrahydropyran, dioxane and the like. The sulfolanes include sulfolane and the like. The organic solvent used in this invention may form a complex with boron trifluoride, and this organic solvent complex with boron trifluoride is also used as the organic solvent in this invention.

The amount of boron trifluoride or its complex compound used may be at least one mole per mole of the compound represented by the general formula (II), or a derivative in the carboxyl group thereof or a salt thereof, and preferably 2 to 7 moles per mole of the latter. When the complex compound is used, it may also be used as a solvent, and a mixture of two or more complex compounds may also be used. In general, it is desirable to vary the amount of boron trifluoride or its complex compound in order to control the reaction rate depending upon the type of solvent and thiol compound or its salt used. The amount of the thiol compound represented by the general formula (III) or its salt used is generally at least one mole per mole of the compound represented by the general formula (II) or a derivative in the carboxyl group thereof or a salt thereof, and preferably 1 to 1.5 moles per mole of the latter. When the compound having >Y being >S→O is used as the starting material, the thiol compound or its salt is preferably used in an amount of 2 to 3 moles per mole of the starting material.

Although no particular limitation is applied to the reaction temperature, the reaction is generally effected at a temperature of −20° to 80° C., and the reaction time is generally several minutes to scores of hours.

In the process of this invention, it is desirable to maintain the reaction system anhydrous, because the presence of water in the reaction system may result in undesirable side reactions such as lactonization of the starting and objective compounds, breakage of β-lactam ring, and the like. For this purpose, the following dehydrating agents may be added to the reaction system: phosphorus compounds such as phosphorus pentachloride, polyphosphoric acid, phosphorus pentoxide, phosphorus trichloride, phosphorus oxychloride and the like; organic silyl compounds such as N,O-bis(trimethylsilyl)acetamide, trimethylsilylacetamide, trimethylchlorosilane, dimethyldichlorosilane and the like; organic acid chlorides, such as acetyl chloride, p-toluenesulfonyl chloride and the like; acid anhydrides, such as acetic anhydride, trifluoroacetic anhydride, and the like; and inorganic compounds for drying, such as anhydrous magnesium sulfate, anhydrous calcium chloride, anhydrous calcium sulfate, molecular sieve, calcium carbide and the like.

The above-mentioned reaction conditions are not limitative and can appropriately be varied depending upon the type of reactants and solvents to achieve the object.

The protecting group

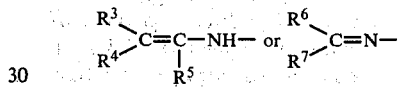

for $R^2$ in the general formula (I) and the protecting group for the carboxylic group in the derivative in the carboxyl group of the compound represented by the general formula (I) can generally be removed by hydrolysis or treatment in a conventional manner to convert the protected groups into an amino group and carboxyl group, respectively. However, in the case where some groups of

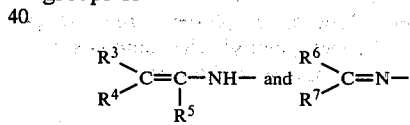

are used or where a certain after-treatment is used the protecting group for amino group is easily removed during the treatment to obtain a compound represented by the general formula (I) in which $R^2$ is an amino group. In the case where the carboxyl group of the compound represented by the general formula (I) is protected with some protecting groups or where a certain after-treatment is used, the protecting group is easily removed during the treatment to convert the protected carboxyl group into a carboxyl group to obtain a compound represented by the general formula (I). When $R^3$, $R^4$, $R^5$, and $R^6$ and $R^7$ are organic residues which do not participate in the reaction and which have a protected hydroxyl, amino, mercapto or carboxyl group as substituent, these groups can be converted into the desired substituents by subjecting the resulting compound to removal reaction in a conventional manner. When the double bond in the cephem ring is present between the 2- and 3-positions the compound can be isomerized into a compound having the double bond between the 3- and 4-positions in a conventional manner. The protecting group-removal reaction and isomerization reaction mentioned above may be effected without isolating the resulting product. The objective compound thus obtained having the general formula (I) can be isolated in a conventional manner.

The objective compound represented by the general formula (I) can directly be used as the starting material for acylation reaction, however it can, if necessary, be converted into highly pure 7-(substituted)amino-3-substituted thiomethyl cephem carboxylic acid in a high yield in a conventional manner.

The following Examples illustrate this invention, but it should be understood that the Examples are merely by way of illustration and not by way of limitation.

EXAMPLE 1

(1) In 14 ml of anhydrous acetonitrile were suspended 2.72 g of 7-aminocephalosporanic acid and 1.16 g of 5-mercapto-1-methyl-1H-tetrazole, and 4.26 g of boron trifluoride-diethyl ether complex was added to the resulting suspension to convert the suspension into a solution. This solution was subjected to reaction at 50° C. for 2 hours. After the completion of the reaction, the reaction solution was cooled, and 14 ml of water was then added. 28% ammonia water was added with ice-cooling to the solution to adjust the pH thereof to 4.0. The crystals thus precipitated were collected by filtration and then washed with 5 ml of water and 5 ml of acetone in this order, and thereafter dried to obtain 3.00 g (yield 91.5%) of 7-amino-3-[5-(1-methyl-1,2,3,4-tetrazolyl)thiomethyl]-$\Delta^3$-cephem-4-carboxylic acid having a melting point of 224°-226° C. (decomp.).

IR (KBr) cm$^{-1}$: 84 $_{C=O}$ 1792, 1610, 1520.

NMR (D$_2$O+CF$_3$CO$_2$D) ppm values:

3.58 (2H, s, C$_2$—CH$_2$), 3.84 (3H, s, >N—CH$_3$),
4.09 (2H, s, C$_3$—CH$_2$), 4.91 (1H, d J=5 cps, C$_6$—H), 5.05 (1H, d J=5 cps, C$_7$—H).

Elementary analysis values (C$_{10}$H$_{12}$N$_6$O$_3$S$_2$):

Calcd. (%) C: 36.59; H: 3.69; N: 25.61.
Found (%) C: 36.54; H: 3.65; N: 25.21.

When other boron trifluoride complexes were substituted for the boron trifluoride-diethyl ether complex in above (1), the following results was obtained.

| Run No. | Boron trilfuoride complex | | Amount (g) | Reaction conditions | Yield (%) |
|---|---|---|---|---|---|
| | Kind | BF$_3$ content (% by weight) | | | |
| 1 | Acetic acid complex | ca 40 | 6.8 | 50° C., 2 hrs. | 82.5 |
| 2 | Phenol complex | ca 25 | 10.9 | 50° C., 2 hrs. | 77.5 |
| 3 | Di-n-butyl ether complex | ca 34 | 6.0 | 50° C., 2 hrs. | 88.7 |
| 4 | Acetic acid complex | ca 40 | 12.4 | 0-5° C., 8 hrs. | 90.5 |

(3) When propionitrile was substituted for the acetonitrile in above (1), the yield was 87.8%.

(4) When sulfolane was substituted for the acetonitrile in above (1), the yield was 90.5% when the reaction was effected at 20° C. for 10 hours.

(5) In above (1), 1.25 ml of 12 N hydrochloric acid was added to the reaction solution with ice-cooling and stirring was continued for 2 hours, and the crystals thus precipitated were then collected by filtration, washed with 5-ml portions of acetone two times and then dried to obtain 3.20 g (yield 88.0%) of 7-amino-3-[5-(1-methyl-1,2,3,4-tetrazolyl)thiomethyl]-$\Delta^3$-cephem-4-carboxylic acid hydrochloride having a melting point of 184°-186° C. (decomp.).

IR (KBr) cm$^{-1}$: $\nu_{C=O}$ 1770, 1710.

NMR (D$_2$O+CF$_3$CO$_2$D): Agreed with standard sample.

Elementary analysis values (C$_{10}$H$_{13}$N$_6$O$_3$S$_2$Cl):

Calcd. (%) C: 32.91; H: 3.59; N: 23.03. Found (%) C: 32.41; H: 3.57; N: 22.71.

EXAMPLE 2

In 11 ml of acetonitrile were suspended 1.1 g of 7-aminocephalosporanic acid and 0.72 g of 5-mercapto-1-phenyl-1H-tetrazole, and 1.7 g of boron trifluoride-diethyl ether complex was added to the resulting suspension to convert the suspension into a solution. This solution was heated at 50° C. for 1 hour and then treated in the same manner as in Example 1 to obtain 1.3 g (yield 82.4%) of 7-amino-3-[5-(1-phenyl-1,2,3,4-tetrazolyl)thiomethyl]-$\Delta^3$-cephem-4-carboxylic acid.

IR (KBr) cm$^{-1}$: 1800 ($\beta$-lactam), 1610, 1530 (carboxylate), 1500 (phenyl).

NMR (D$_2$O+CF$_3$CO$_2$D) ppm values: 3.75 (2H, s, C$_2$—CH$_2$), 4.61, 4.35 (2H, ABq J=14 cps, C$_3$—CH$_2$), 5.20 (2H, m, C$_7$—H, C$_6$—H), 7.58 (5H, s, phenyl).

Elementary analysis values (C$_{15}$H$_{14}$N$_6$O$_3$S$_2$): Calcd. (%) C: 46.16; H: 3.62; N: 21.53. Found (%) C: 46.74; H: 3.62; N: 21.40.

EXAMPLE 3

In 54 ml of acetonitrile were suspended 5.44 g of 7-aminocephalosporanic acid and 3.00 g of 2-mercaptobenzoxazole, and 8.52 g of boron trifluoride-diethyl ether complex was added thereto to convert the suspension into a solution. This solution was heated at 60° C. for one hour to subject it to reaction, and the resulting reaction solution was treated in the same manner as in Example 1 to obtain 6.80 g (yield 81.1%) of 7-amino-3-[2-(benzoxazolyl)thiomethyl]-$\Delta^3$-cephem-4-carboxylic acid having a melting point of 210°-212° C. (decomp.).

IR (KBr) cm$^{-1}$: $\nu_{C=O}$ 1790, 1600, 1495.

NMR (D$_2$O+CF$_3$CO$_2$D) ppm values: 3.83 (2H, s, C$_2$—CH$_2$), 4.64 (2H, s, C$_3$—CH$_2$), 5.25 (2H, m, C$_7$—H, C$_6$—H), 7.53 (4H, m, >C$_6$H$_4$).

EXAMPLE 4

(1) In 27 ml of acetic acid were suspended 2.72 g of 7-aminocephalosporanic acid and 1.16 g of 5-mercapto-1-methyl-1H-tetrazole, and 4.26 g of boron trifluoride-diethyl ether complex was added to the suspension to convert it to a solution. This solution was heated at 50° C. for two hours. After the completion of the reaction, the solvent was removed by distillation under reduced pressure, and to the residue were added 16 ml of acetone and 16 ml of water to dissolve the residue. The resulting solution was cooled with ice and the pH of the solution was adjusted to 4.0 with 28% ammonia water. The crystals thus precipitated were collected by filtration, washed with 5 ml of water and then 5 ml of acetone, and thereafter dried to obtain 2.80 g (yield 85.5%) of 7-amino-3-[5-(1-methyl-1,2,3,4-tetrazolyl)thiomethyl]-$\Delta^3$-cephem-4-carboxylic acid.

(2) When nitromethane was substituted for the acetic acid in above (1), the yield was 82.5%.

(3) When other boron trifluoride complexes were substituted for the boron trifluoride-diethyl ether complex in above (1), the results obtained were as follows:

| Run No. | Boron trifluoride complex Kind | BF₃ content (% by weight) | Amount (g) | Yield (%) |
|---|---|---|---|---|
| 1 | Acetic acid complex | ca 40 | 6.8 | 84.7 |
| 2 | Phenol complex | ca 25 | 10.9 | 79.8 |
| 3 | Di-n-butyl ether complex | ca 34 | 6.0 | 84.7 |

EXAMPLE 5

In 27 ml of acetic acid were suspended 2.72 g of 7-aminocephalosporanic acid and 1.33 g of 2-methyl-5-mercapto-1,3,4-thiadiazole, and 9.64 g of boron trifluoride-diethyl ether complex was added to the resulting suspension to convert the suspension into a solution. This solution was heated at 55° C. for 30 minutes to subject it to reaction, and then treated in the same manner as in Example 4 to obtain 2.96 g (yield 86.1%) of 7-amino-3-[2-(5-methyl-1,3,4-thiadiazolyl)thiomethyl]-$\Delta^3$-cephem-4-carboxylic acid having a melting point of 199°–200° C. (decomp.).

IR (KBr) cm$^{-1}$: $\nu_{C=O}$ 1790, 1610, 1520.

NMR (D$_2$O+CF$_3$CO$_2$D) ppm values: 3.88 (3H, s, —CH$_3$), 3.75 (2H, s, C$_2$—CH$_2$), 4.33, 4.61 (2H, ABq J=14 cps, C$_3$—CH$_2$), 5.20 (2H, m, C$_6$—H, C$_7$—H).

Elementary analysis values (C$_{11}$H$_{12}$N$_4$O$_3$S$_3$): Calcd. (%) C: 38.38; H: 3.51; N: 16.28. Found (%) C: 37.80; H: 3.41; N: 15.71.

EXAMPLE 6

In 27 ml of acetic acid were suspended 2.72 g of 7-aminocephalosporanic acid and 1.00 g of 5-mercapto-1,2,3-triazole, and 9.64 g of boron trifluoride-diethyl ether complex was added to the resulting suspension to convert the suspension into a solution. This solution was heated at 55° C. for one hour to subject it to reaction, and then treated in the same manner as in Example 4 to obtain 2.56 g (yield 82.1%) of 7-amino-3-[5-(1,2,3-triazolyl)thiomethyl]-$\Delta^3$-cephem-4-carboxylic acid having a melting point of 209° C. (decomp.).

IR (KBr) cm$^{-1}$: $\nu_{C=O}$ 1800, 1610, 1520.

NMR (D$_2$O+CF$_3$CO$_2$D) ppm values: 5.79–4.45 (4H, m, C$_2$—CH$_2$, C$_3$—CH$_2$), 5.15 (1H, d J=5 cps, C$_6$—H), 5.28 (1H, d J=5 cps, C$_7$—H), 8.28 (1H, s, C-H in triazolyl group).

EXAMPLE 7

In 5 ml of acetic acid were suspended 1.0 g of 7-aminocephalosporanic acid and 0.55 g of 2-mercaptobenzimidazole, and 2.0 g of boron trifluoride-diethyl ether complex was added to the resulting suspension to convert the suspension into a solution. This solution was heated at 50° C. for two hours to subject it to reaction, and then treated in the same manner as in Example 4 to obtain 1.0 g (yield 75.2%) of 7-amino-3-[2-(benzimidazolyl)thiomethyl]-$\Delta^3$-cephem-4-carboxylic acid having a melting point of 230° C. or more.

IR (KBr) cm$^{-1}$: $\nu_{C=O}$ 1800, 1620, 1530.

NMR (D$_2$O+CF$_3$CO$_2$D) ppm values: 3.93 (2H, s, C$_2$—CH$_2$), 4.76, 4.44 (2H, ABq J=12 cps, C$_3$—CH$_2$), 5.20–5.32 (2H, m, C$_7$—H, C$_6$—H), 7.65 (4H, m, phenyl).

EXAMPLE 8

In 10 ml of acetic acid were suspended 1.10 g of 7-aminocephalosphoranic acid and 0.305 g of propane thiol, and 2.0 ml of boron triflurodie-acetic acid complex (BF$_3$ content, about 40% by weight; specific gravity, 1.351) was added to the resulting suspension to convert it into a solution. This solution was heated at 50° C. for one hour to subject it to reaction, and then treated in the same manner as in Example 4 to obtain 0.98 g (yield 84.3%) of 7-amino-3-propylthiomethyl-$\Delta^3$-cephem-4-carboxylic acid having a melting point of 215° C. or more.

IR (KBr) cm$^{-1}$: $\nu_{C=O}$ 1795, 1610, 1520.

NMR (D$_2$O+CF$_3$CO$_2$D) ppm values: 0.95 (3H, t J=7 cps, —CH$_2$CH$_2$CH$_3$), 1.59 (2H, m, —CH$_2$CH$_2$CH$_3$), 2.52 (2H, t J=7 cps, —CH$_2$CH$_2$CH$_3$), 3.66 (2H, s, C$_2$—CH$_2$), 3.77 (2H, s, C$_3$—CH$_2$), 5.10 (1H, d J=6 cps, C$_6$—H), 5.27 (1H, d J=6 cps, C$_7$—H).

Elementary analysis values (C$_{11}$H$_{16}$N$_2$O$_3$S$_2$): calcd. (%) C: 45.83; H: 5.60; N: 9.72. Found (%) C: 44.79; H: 5.27; N: 9.55.

EXAMPLE 9

The same procedure as in Example 8 was repeated, except that 0.44 g of thiophenol was substituted for the propane thiol, to obtain 1.08 g (yield 83.1%)of 7-amino-3-phenylthiomethyl-$\Delta^3$-cephem-4-carboxylic acid having a melting point of 235° C. or more.

IR (KBr) cm$^{-1}$: $\nu_{C=O}$ 1785, 1610, 1520.

NMR (D$_2$O+CF$_3$COOD)ppm values: 3.52 (2H, s, C$_2$—CH$_2$), 4.35, 3.79 (2H, ABq J=14 cps, C$_3$—CH$_2$), 5.01 (2H, m, C$_6$—H, C$_7$—H), 7.30 (5H, m, phenyl).

Elementary analysis values (C$_{14}$H$_{14}$N$_2$O$_3$S$_2$): Calcd. (%) C: 52.17; H: 4.38; N: 8.69. Found (%) C: 52.20; H: 4.36; N: 8.60.

EXAMPLE 10

In 50 ml of acetic acid were suspended 4.81 g of the dihydrate of p-toluenesulfonic acid salt of 7-aminocephalosporanic acid and 1.16 g of 5-mercapto-1-methyl-1H-tetrazole, and 7.10 g of boron trifluoride-diethyl ether complex was added to the resulting suspension to convert the suspension into a solution. This solution was heated at 55° C. for one hour to subject it to reaction, and then treated in the same manner as in Example 4 to obtain 2.49 g (yield 77.3%) of 7-amino-3-[5-(1-methyl-1,2,3,4-tetrazolyl)thiomethyl]-$\Delta^3$-cephem-4-carboxylic acid. The IR, NMR and melting point of this product were identical with those of the standard sample.

EXAMPLE 11

In 50 ml of anhydrous acetonitrile were suspended 5.80 g of (1R)-7-amino-3-acetoxymethyl-$\Delta^3$-cephem-4-carboxylic acid 1-oxide and 4.66 g of 5-mercapto-1-methyl-1H-tetrazole, and 15.4 g of boron trifluoride-acetic acid complex (BF$_3$ content, about 40% by weight) was added to the resulting suspension to convert the suspension into a solution. This solution was subjected to reaction at 20° C. for 12 hours, and the resulting reaction solution was cooled with ice, after which 50 ml of water was added thereto. The pH of the solution was adjusted to 4.0 with 28% ammonia water. The crystals thus precipitated were collected by filtration, washed with 5 ml of water and then 5 ml of acetone, and thereafter dried to obtain 5.28 g of crude crystals. The crude crystals were dissolved in a mixture of 25 ml of 2 N hydrochloric acid and 25 ml of methanol and subjected to carbon treatment, after which the pH of the solution was adjusted to 4.0 with 28% ammonia water. The crystals thus precipitated were collected by filtration, washed and then dried to obtain 5.05 g (yield 76.4%) of 7-amino-3-[5-(1-methyl-1,2,3,4-tetrazolyl)thiomethyl]-Δ³-cephem-4-carboxylic acid. The IR, NMR and melting point of this product were identical with those of the standard sample.

EXAMPLE 12

In 50 ml of anhydrous acetonitrile were suspended 5.30 g of 7-amino-3-acetoxymethyl-Δ²-cephem-4-carboxylic acid and 2.26 g of 5-mercapto-1-methyl-1H-tetrazole, and 5.84g of boron trifluoride-acetic acid complex (BF₃ content, about 40% by weight) was added to the resulting suspension to convert the suspension into a solution. This solution was subjected to reaction at 20° C. for 12 hours, and the solvent was then removed by distillation under reduced pressure. To the residue were added 45 ml of methanol and 5 mlof water to dissolve the residue, and the pH of the resulting solution was adjusted to 4.0 with 28% ammonia water with ice-cooling. The crystals thus precipitated were collected by filtration, washed with 5 ml of water, then 5 ml of 90% methanol and then 5 ml of acetone, and thereafter dried to obtain 5.14 g (yield 80.5%) of 7-amino-3-[5-(1-methyl-1,2,3,4-tetrazolyl)thiomethyl]-Δ²-cephem-4-carboxylic acid crystals having a melting point of 105°–108° C. (decomp.).

IR (KBr) cm⁻¹: $\nu_{C=O}$ 1770, 1608.

NMR (D₂O+CF₃CO₂D) ppm values: 3.93 (3H, s, >N—CH₃), 4.12 (2H, s, C₃—CH₂), 4.96 (1H, d J=5 cps, C₆—H), 5.25 (1H, bs, C₄—H), 5.38 (1H, d J=5 cps, C₇—H), 6.38 (1h, bs, C₂—H).

EXAMPLE 13

In 5.5 ml of boron trifluoride-acetic acid complex (BF₃ content, about 40% by weight; specific gravity, 1.351) were dissolved 1.1 g of 7-amino-cephalosporanic acid and 0.46 g of 5-mercapto-1-methyl-1H-tetrazole, and this solution was heated at 50° C. for one hour to subject it to reaction. After the completion of the reaction, 5 ml of water and 5 ml of acetone were added to the resulting reaction solution, and the pH of the solution was adjusted to 4.0 with 28% ammonia water with ice-cooling. The crystals thus precipitated were collected by filtration, washed with 2 ml of water and then 2 ml of acetone, and thereafter dried to obtain 1.02 g (yield 76.7%) of 7-amino-3-[5-(1-methyl-1,2,3,4-tetrazolyl)thiomethyl]-Δ³-cephem-4-carboxhlic acid. The IR, NMR and melting point of this product were identical with those of the standard sample.

EXAMPLE 14

In 6.7 ml of acetonitrile were suspended 0.67 g of the hydrochloric acid salt of ethyl 7-amino-3-acetoxymethyl-Δ²-cephem-4-carboxylate and 0.23 g of 5-mercapto-1-methyl-1H-tetrazole, and 0.9 ml of boron trifluoride-acetic acid complex (BF₃ content, about 40% by weight; specific gravity, 1.351) was added to the resulting suspension to convert the suspension into a solution. This solution was subjected to reaction at room temperature for 30 minutes, and thereafter, the solvent was removed by distillation under reduced pressure. To the resulting residue were added 5 ml of methylene chloride and 10 ml of water to dissolve the residue, and the pH of the resulting solution was adjusted to 7.0 with sodium hydrogen carbonate with ice-cooling. The organic layer was separated, and the organic liquid particles in the aqueous layer were collected by extraction with 5 ml methylene chloride and then combined with the above organic layer. The organic layer obtained was washed with water and then dried on anhydrous magnesium sulfate, after which the solvent was removed by distillation under reduced pressure. To the resulting residue was added 5 ml of ethyl acetate to dissolve the residue, and to the resulting solution was added a mixture of 0.38 g of p-toluenesulfonic acid monohydrate, 2 ml of ethyl acetate and 1 ml of methanol. The resulting solution was stirred at room temperature for one hour, and the crystals thus precipitated were collected by filtration to obtain 0.88 g (yield 83.5%) of the p-toluenesulfonic acid salt of ethyl 7-amino-3-[5-(1-methyl-1,2,3,4-tetrazolyl)thiomethyl]-Δ²-cephem-4carboxylate having a melting point of 147°–149° C. (decomp.).

IR (KBr) cm⁻¹: $\nu_{C=O}$ 1790, 1730.

NMR (CDCl₃) ppm values: 1.22 (3H, t J=7 cps, —CH₂—CH₃),

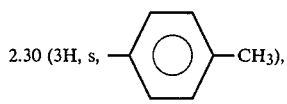
2.30 (3H, s, —C₆H₄—CH₃), 3.78 (3H, s, >N—CH₃), 3.95–4.25 (5H, m, C₄—H+C₃—CH₂+—CH₂—CH₃), 4.97 (1H, d J=5 cps, C₆—H), 5.20 (1H, d J=5 cps, C₇—H), 6.25 (1H, s, C₂—H), 7.63,

7.03 (4H, ABq J = 9 cps, —C₆H₄—)

Elementary analysis values (C₁₉H₂₄N₆O₆S₃): Calcd. (%) C: 43.15; H: 4.54; N: 15.90. Found (%) C: 43.13; H: 4.57; N: 15.84.

EXAMPLE 15

In 4.7 ml of acetonitrile were dissolved 0.47 g of the p-toluenesulfonic acid salt of ethyl 7-aminocephalosporanate and 0.12 g of 5-mercapto-1-methyl-1H-tetrazole, and 0.4 ml of boron trifluorideacetic acid complex (BF₃ content, about 40% by weight) was added to the resulting solution, and the resulting solution was subjected to reaction at room temperature for 7 hours. The solvent was removed by distillation under reduced pressure, and 5 ml of methylene chloride and 5 ml of water were added to the resulting residue to dissolve the residue. The pH of the resulting solution was adjusted to 7.0 by adding sodium hydrogen carbonate with ice-cooling, and the organic layer was separated, washed with water and then dried on anhydrous magnesium sulfate. To the organic layer thus obtained was added a solution of 0.19 g of p-toluenesulfonic acid monohydrate in 1 ml of methanol, and the solvent was then removed by distillation under reduced pressure. To the resulting residue was added diethyl ether and the undissolved portion was collected by filtration to obtain 0.44 g (yield 83.3%) of the p-toluenesulfonic acid salt of ethyl 7-amino-3-[5-(1-methyl-1,2,3,4-tetrazolyl)thiomethyl]-Δ³-cephem-4-carboxylate having a melting point of 115°–122° C. (decomp.).

IR (KBr) cm⁻¹: $\nu_{C=O}$ 1790, 1715.

NMR (CDCl₃) ppm values: 1.23 (3H, t J=6 cps, —CH₂—CH₃), 2.30 (3H, s, —C₆H₄—CH₃), 3.45 (2H, s, C₂—CH₂), 3.81 (3H, s, >N—CH₃), 4.30, 4.04 (2H, ABq J=10 cps, C₃—CH₂), 4.95 (2H, m, C₇—H, C₆—H), 7.01, 7.59 (4H, ABq J=8 cps, >C₆H₄), 8.37 (2H, br, —NH₂)

EXAMPLE 16

In 3.0 ml of acetonitrile were suspended 0.30 g of the p-toluenesulfonic acid salt of diphenylmethyl 7-aminocephalosporanate and 0.06 g of 5-mercapto-1-methyl-1H-tetrazole, and 0.2 ml of boron trifluoride-diethyl ether complex (specific gravity, 1.125) was added to the resulting suspension to convert the suspension into a solution. This solution was subjected to reaction at room temperature overnight. The solvent of the resulting reaction solution was removed by distillation under reduced pressure, and 2 ml of water and 2 ml of acetone were added to the resulting residue, after which the resulting solution was stirred for 30 minutes with ice-cooling. The pH of the solution was then adjusted to 4.0 by adding 28% ammonia water, and the crystals thus precipitated were collected by filtration, washed with 3 ml of water and then 3 ml of acetone, and thereafter dried to obtain 0.13 g (yield 80.6%) of 7-amino-3-[5-(1-methyl-1,2,3,4-tetrazolyl)thiomethyl]-$\Delta^3$-cephem-4-carboxylic acid. The IR, NMR and melting point of this product were identical with those of the standard sample.

EXAMPLE 17

In 11 ml of acetic acid were suspended 1.1 g of 7-aminocephalosporanic acid and 0.61 g of the sodium salt of 1-ethyl-5-mercapto-1,2,3,4-tetrazole, and 1.7 g of boron trifluoride-diethyl ether complex was added to the resulting suspension to convert the suspension into a solution. This solution was subjected to reaction at 50° C. for two hours. After the completion of the reaction, the reaction solution was treated in the same manner as in Example 4 to obtain 1.20 g (yield 86.8%) of 7-amino-3-[5-(1-ethyl-1,2,3,4-tetrazolyl)thiomethyl]-$\Delta^3$-cephem-4-carboxylic acid having a melting point of 201°–203° C. (decomp.).

IR (KBr) cm$^{-1}$: $\nu_{C=O}$ 1785, 1610, 1530.

NMR (D$_2$O+CF$_3$CO$_2$D) ppm values: 1.55 (3H, t J=7 cps, —CH$_2$—CH$_3$), 3.81 (2H, s, C$_2$—CH$_2$), 4.35 (2H, s, C$_3$—CH$_2$), 4.42 (2H, q J=7 cps, —CH$_2$—CH$_3$), 5.15 (1H, d J=5 cps, C$_6$—H), 5.28 (1H, d J=5 cps, C$_7$—H)

EXAMPLE 18

In 14 ml of anhydrous acetonitrile were suspended 2.72 g of 7-aminocepharosporanic acid and 1.16 g of 5-mercapto-1-methyl-1H-tetrazole, and 2.0 g of boron trifluoride was added to the suspension at a temperature of −5° to 5° C. to convert the suspension into a solution. This solution was heated at 30° C. for one hour to subject it to reaction, and thereafter treated in the same manner as in Example 1 (1) to obtain 3.08 g (yield 93.9%) of 7-amino-3-[5-(1-methyl-1,2,3,4-tetrazolyl)thiomethyl]-$\Delta^3$-cephem-4-carboxylic acid. The IR, NMR and melting point of this product were identical with those of the standard sample.

EXAMPLE 19

In 14 ml of nitromethane were suspended 2.72 g of 7-aminocephalosporanic acid and 1.33 g of 2-methyl-5-mercapto-1,3,4-thiadiazole, and 3.5 g of boron trifluoride was added to the resulting suspension at a temperature of 0° to 8° C. to convert the suspension into a solution. This solution was subjected to reaction at room temperature for two hours, and the resulting reaction solution was then cooled and diluted with 15 ml of water, after which the pH of the solution was adjusted to 4.0 with 28% ammonia water with ice-cooling. The crystals thus precipitated were collected by filtration, washed with 5 ml of water and then 5 ml of acetone, and thereafter dried to obtain 2.97 g (yield 86.3%) of 7-amino-3-[2-(5-methyl-1,3,4-thiadiazolyl)thiomethyl]-$\Delta^3$-cephem-4-carboxylic acid. The IR, NMR and melting point of this product were identical with those of the standard sample.

EXAMPLE 20

In 30 ml of anhydrous acetonitrile were suspended 10.0 g of 7-aminocephalosporanic acid and 4.34 g of 5-mercapto-1,3,4-thiadiazole, and 8.0 g of boron trifluoride and 50 ml of anhydrous acetonitrile were added to the resulting suspension at a temperature of 0° to 5° C. to convert the suspension into a solution. This solution was subjected to reaction at 25° C. for 2.5 hours, and thereafter treated in the same manner as in Example 1 (1) to obtain 10.7 g (yield 88.4%) of 7-amino-3-[5-(1,3,4-thiadiazolyl)thiomethyl]-$\Delta^3$-cephem-4-carboxylic acid having a melting point of 202°–204° C. (decomp.).

IR (KBr) cm$^{-1}$: $\nu_{C=O}$ 1790, 1610, 1530.

NMR (D$_2$O+CF$_3$COOD) ppm values: 3.75 (2H, s, C$_2$—CH$_2$), 4.37, 4.55 (2H, ABq J=14 cps, C$_3$—CH$_2$), 5.05–5.24 (2H, m, C$_6$—H, C$_7$—H),

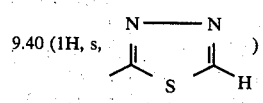

EXAMPLE 21

In the same manner as in Example 18, 2.72 g of 7-aminocephalosporanic acid was reacted with 1.60 g of 5-mercapto-1-carboxymethyl-1,2,3,4-tetrazole, and the resulting reaction solution was treated in the same manner as in Example 18 to obtain 3.1 g (yield 83.3%) of 7-amino-3-[5-(1-carboxymethyl-1,2,3,4-tetrazolyl)thiomethyl]-$\Delta^3$-cephem-4-carboxylic acid having a melting point of 183° C. (decomp.).

IR (KBr) cm$^{-1}$: $\nu_{C=O}$ 1800, 1735, 1615, 1520.

NMR (D$_2$O+CF$_3$COOD) ppm values: 3.76 (2H, s, C$_2$—CH$_2$), 4.41 (2H, s, C$_3$—CH$_2$), 5.22 (1H, d J=6 cps, C$_6$—H), 5.24 (1H, d J=6 cps, C$_7$—H),

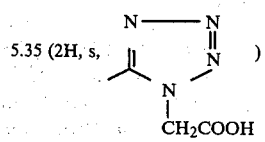

EXAMPLE 22

When in the same manner as in Example 1, 7-aminocephalosporanic acid, a suitable thiol compound represented by the general formula (III), and boron trifluoride or boron trifluoride-diethyl ether complex are subjected to reaction using acetonitrile or acetic acid as the solvent, the following compounds are obtained in a yield of 75 to 90% or more:

7-amino-3-[5-(1-sulfomethyl-1,2,3,4-tetrazolyl)thiomethyl]-$\Delta^3$-cephem-4-carboxylic acid, 7-amino-3-[2-(5-methyl-1,3,4-oxadiazolyl)-thiomethyl]-$\Delta^3$-cephem-4-carboxylic acid, 7-amino-3-[2-(5-ethyl-1,3,4-thiadiazolyl)-thiomethyl]-$\Delta^3$-cephem-4-carboxylic acid, 7-amino-3-[2-(5-methyl-1,3-thiazolyl)thiomethyl)]-Δ³-cephem-4-carboxylic acid, 7-amino-3-[2-(5-methyl-1,3-oxazolyl)thiomethyl)]-Δ³-cephem-4-carboxylic acid, 7-amino-3-[2-(1-methyl-1,3,4-triazolyl)thiomethyl]-Δ³-cephem-4-carboxylic acid, 7-amino-3-[2-(1,3-thiazolyl)thiomethyl]-Δ³-cephem-4-carboxylic acid, 7-amino-3-[2-(5-amino-1,3,4-thiadiazolyl)thiomethyl]-Δ³-cephem-4-carboxylic acid, 7-amino-3-[2-(5-phenyl-1,3,4-thiadiazolyl)thiomethyl]-Δ³-cephem-4-carboxylic acid, 7-amino-3-[5-(3-methyl-1,2,4-thiadiazolyl)-thiomethyl]-Δ³-cephem-4-carboxylic acid, 7-amino-3-[5-(1,2,3,4-thiatriazolyl)thiomethyl]-Δ³-cephem-4-carboxylic acid, 7-amino-3-[2-(5-methyl-1,3,4-triazolyl)thiomethyl]-Δ³-cephem-4-carboxylic acid, 7-amino-3-[2-(1,5-dimethyl-1,3,4-triazolyl)thiomethyl]-Δ³-cephem-4-carboxylic acid, 7-amino-3-(2-imidazolylthiomethyl)-Δ³-cephem-4-carboxylic acid, 7-amino-3-[4-(5-ethoxycarbonyl-1,2,3-triazolyl)-thiomethyl]-Δ³-cephem-4-carboxylic acid, 7-amino-3-[4-(5-carboxy-1,2,3-triazolyl)thiomethyl]-Δ³-cephem-4-carboxylic acid, 7-amino-3-[2-(5-ethoxycarbonylmethyl-1,3,4-triazolyl)-thiomethyl]-Δ³-cephem-4-carboxylic acid, 7-amino-3-{5-[2-(2-carbamoylethyl)-1,2,3,4-tetrazolyl]-thiomethyl}-Δ³-cephem-4-carboxylic acid, 7-amino-3-[2-(5-carboxymethyl-1,3,4-thiadiazolyl)-thiomethyl]-Δ³-cephem-4-carboxylic acid, 7-amino-3-{5-[1-(2-sulfamoylethyl)-1,2,3,4-tetrazolyl]-thiomethyl}-Δ³-cephem-4-carboxylic acid, 7-amino-3-{5-[1-(2-N,N-dimethylaminoethyl)-1,2,3,4-tetrazolyl]thiomethyl}-Δ³-cephem-4-carboxylic acid, 7-amino-3-{5-[1-(2-N,N-diethylaminoethyl)-1,2,3,4-tetrazolyl]thiomethyl}-Δ³-cephem-4carboxylic acid, 7-amino-7-αmethoxy-3-[2-(5-methyl-1,3,4-thiadiazolyl)-thiomethyl]-Δ³-cephem-4-carboxylic acid, 7-amino-7-α-methoxy-3-[5-(1-methyl-1,2,3,4-tetrazolyl)thiomethyl]-Δ³-cephem-4-carboxylic acid, 7-amino-3-[5-(1-vinyl-1,2,3,4-tetrazolyl)]-thiomethyl-Δ³-cephem-4-carboxylic acid, and 7-amino-3-{5-[2-(2-N,N-dimethylaminoethyl)-1,2,3,4-tetrazolyl]thiomethyl}-Δ³-cephem-4-carboxylic acid.

EXAMPLE 23

In 3 ml of anhydrous acetonitrile were suspended 1.0 g of 7-aminocephalosporanic acid and 0.58 g of 5-mercapto-1-carbamoylmethyl-1H-tetrazole, and 5 ml of acetonitrile containing 0.80 g of boron trifluoride was added to the resulting suspension at a temperature of 0° to 5° C. to convert the suspension into a solution. This solution was subjected to reaction at 25° C. for 2.5 hours, and thereafter treated in the same manner as in Example 1 to obtain 1.25 g (yield 91.9%) of 7-amino-3-[5-(1-carbamoylmethyl-1,2,3,4-tetrazolyl)thiomethyl]-Δ³-cephem-4-carboxylic acid having a melting point of 189°–190.5° C. (decomp.).

IR (KBr) cm$^{-1}$: $\nu_{C=O}$ 1790, 1680, 1610, 1530.

NMR (D$_2$O+CF$_3$COOD) ppm values: 3.73 (2H, s, C$_2$—CH$_2$), 4.28, 4.37 (2H, ABq J=14 cps, C$_3$—CH$_2$), 5.03–5.23 (4H, m, >N—CH$_2$CONH$_2$, C$_6$—H, C$_7$—H).

In the same manner as above, 0.48 g of 7-aminocephalosporanic acid was reacted with 0.26 g of 5-mercapto-1-hydroxyethyl-1H-tetrazole to obtain 0.56 g (yield 88.9%) of 7-amino-3-{5-[1-(2-hydroxyethyl)-1,2,3,4-tetrazolyl]thiomethyl}-Δ³-cephem-4-carboxylic acid having a melting point of 190°–192° C. (decomp.).

IR (KBr) cm$^{-1}$: $\nu_{C=O}$ 1795, 1610, 1540.

NMR (D$_2$O+CF$_3$COOD) ppm values: 3.89 (2H, s, C$_2$—CH$_2$), 4.12 (2H, t J=5 cps, —CH$_2$OH), 4.48 (2H, s, C$_3$—CH$_2$),

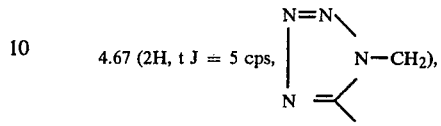

4.67 (2H, t J = 5 cps, 5.30 (1H, d J=5 cps, C$_6$—H), 5.37 (1H, d J=5 cps, C$_7$—H.

When 0.5 g of 7-aminocephalosporanic acid is reacted with 0.15 g of 5-mercapto-1,2,3,4-1H-tetrazole, 0.35 g (yield 77.4%) of 7-amino-3[5-(1,2,3,4-tetrazolyl)thiomethyl]-Δ³-cephem-4-carboxylic acid is obtained.

IR (KBr) cm$^{-1}$: $\nu_{C=O}$ 1800, 1610, 1525.

NMR (D$_2$O+CF$_3$COOD) ppm values: 3.80 (2H, s, C$_2$—H), 4.35 (2H, ABq J=10 cps, C$_3$—CH$_2$), 5.19–5.24 (2H, m, C$_6$—H, C$_7$—H).

EXAMPLE 24

In the same manner as in Example 18, 5.4 g of 7-aminocephalosporanic acid was reacted with 2.4 g of ethyl thioglycolate and the resulting reaction solution was treated in the same manner as in Example 18 to obtain 5.4 g (yield 82.2%) of 7-amino-3-(ethoxycarbonylmethylthiomethyl)-Δ³-cephem-4-carboxylic acid having a melting point of 208°–210° C. (decomp.).

IR (KBr) cm$^{-1}$: $\nu_{C=O}$ 1800, 1715, 1610, 1520.

NMR (D$_2$O+CF$_3$COOD) ppm values: 1.29 (3H, t J=7 cps, —CH$_2$CH$_3$), 3.41 (2H, s, —CH$_2$COOEt), 3.74 (2H, s, C$_2$—CH$_2$), 3.85, 3.95 (2H, ABq J=7 cps, C$_3$—CH$_2$), 4.20 (2H, q J=7 cps, —CH$_2$CH$_3$), 5.16 (1H, d J=5 cps, C$_6$—H), 5.33 (1H, d J=5 cps, C$_7$—H).

In the same manner as above, 2.72 g of 7-aminocephalosporanic acid was reacted with 1.0 g of thioglycolic acid to obtain 2.5 g (yield 80.1%) of 7-amino-3-(carboxymethylthiomethyl)-Δ³-cephem-4-carboxylic acid having a melting point of 193°–196° C. (decomp.).

IR (KBr) cm$^{-1}$: $\nu_{C=O}$ 1775, 1695, 1610, 1510.

NMR (D$_2$O+CF$_3$COOD) ppm values: 3.41 (2H, s, —CH$_2$COOH), 3.71 (2H, s, C$_2$—CH$_2$), 3.59, 4.04 (2H, ABq J=14 cps, C$_3$—CH$_2$), 5.10 (1H, d J=5 cps, C$_6$—H), 5.25 (1H, d J=5 cps, C$_7$—H).

EXAMPLE 25

In 2 ml of anhydrous acetonitrile were suspended 0.54 g of 7-aminocephalosporanic acid and 0.36 g of 5-mercapto-1-(β-aminoethyl)-1H-tetrazole hydrochloride, and 3.6 ml of acetonitrile containing 0.57 g of boron trifluoride was added to the resulting suspension at a temperature of 0° to 5° C. to convert the suspension into a solution. This solution was subjected to reaction at 25° C. for 2.5 hours, and thereafter treated in the same manner as in Example 1 to obtain 0.56 g (yield 78.8%) of 7-amino-3-{5-[1-(2-aminoethyl)-1,2,3,4-tetrazolyl]thiomethyl}-Δ³-cephem-4-carboxylic acid having a melting point of 204°–207° C. (decomp.).

IR (KBr) cm$^{-1}$: $\nu_{C=O}$ 1790, 1610, 1525.

NMR (D$_2$O+CF$_3$COOD) ppm values: 3.67 (2H, t J=6 cps, —CH$_2$NH$_2$), 3.80 (2H, s, C$_2$—CH$_2$), 4.29, 4.31 (2H, ABq J=14 cps, C$_3$—CH$_2$),

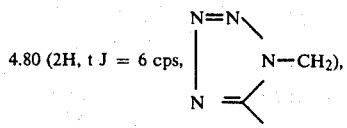

4.80 (2H, t J = 6 cps, 5.13 (1H, d J=5 cps, C$_6$—H), 5.26 (1H, d J=5 cps, C$_7$—H).

EXAMPLE 26

(1) In 3 ml of acetic acid were suspended 0.40 g of sodium 7-(2-hydroxybenzylideneamino)cephalosporanate and 0.12 g of 5-mercapto-1-methyl-1H-tetrazole, and 0.70 g of boron trifluoride-acetic acid complex was added to the resulting suspension to convert the suspension into a solution. This solution was then subjected to reaction at room temperature for five hours. The solvent was removed by distillation under reduced pressure, and 5 ml of acetone and 5 ml of water were added to the resulting residue to dissolve the residue. The pH of the resulting solution was adjusted to 7.0 by adding sodium hydrogen carbonate powder gradually to the solution. The crystals thus precipitated were collected by filtration, washed with 1 ml of water and then 2 ml of acetone, and thereafter dried to obtain 0.42 g (yield 92%) of sodium 7-(2-hydroxybenzylideneamino)-3-[5-(1-methyl-1,2,3,4-tetrazolyl)thiomethyl[-$\Delta^3$-cephem-4-carboxylate.

IR (KBr) cm$^{-1}$: $\nu_{C=O}$ 1760, 1625, 1595.

NMR (d$_6$-DMSO+D$_2$O) ppm values: 3.75 (2H, s, C$_2$—H), 3.95 (3H, s, >N—CH$_3$), 4.1–4.40 (2H, m, C$_3$—CH$_2$), 5.27 (1H, d, C$_5$—H), 5.50 (1H, d, C$_6$—H), 6.85–7.57 (4H, m, aromatic proton), 8.18 (1H, s, —CH=N—).

When the boron trifluoride-acetic acid complex was replaced by other boron trifluoride complexes, the following results were obtained:

| | |
|---|---|
| Boron trifluoride-diethyl ether complex: | Yield 93.0% |
| Boron trifluoride-dibutyl ether complex: | Yield 89.0% |

(2) In a liquid mixture of 3 ml of 4 N hydrochloric acid and 3 ml of diethyl ether, 0.39 g of the sodium 7-(2-hydroxybenzylideneamino)-3-[5-(1-methyl-1,2,3,4-tetrazolyl)thiomethyl]-$\Delta^3$-cephem-4-carboxylate obtained in above (1) was stirred for one hour. The aqueous layer was thereafter separated and washed with 3 ml portions of diethyl ether twice, after which concentrated ammonia water was added thereto with ice-cooling to adjust the pH thereof to 3.7. The crystals thus precipitated were collected by filtration, washed with water and then dried to obtain 0.23 g (yield 82.1%) of 7-amino-3-[5-(1-methyl-1,2,3,4-tetrazolyl)thiomethyl]-$\Delta^3$-cephem-4-carboxylic acid. The melting point, IR and NMR of this product were identical with those of the standard sample.

EXAMPLE 27

To a mixture of 0.40 g of sodium 7-(2-hydroxybenzylideneamino)cephalosporanate, 0.12 g of 5-mercapto-1-methyl-1,2,3,4-tetrazole and 5 ml of acetonitrile was added 0.2 g of boron trifluoride with ice-cooling. The resulting mixture was subjected to reaction at room temperature for one hour, and the solvent was thereafter removed by distillation under reduced pressure. To the resulting residue were added 5 ml of water and 5 ml of acetone to dissolve the residue, and sodium hydrogen carbonate was added to the resulting solution to adjust the pH thereof to 7.0. The crystals thus precipitated were collected by filtration, washed with 1 ml of water and then 2 ml of acetone, and thereafter dried to obtain 0.43 g (yield 94.3%) of sodium 7-(2-hydroxybenzylideneamino)-3-[5-(1-methyl-1,2,3,4-tetrazolyl)thiomethyl]-$\Delta^3$-cephem-4-carboxylate.

EXAMPLE 28

In 2 ml of acetonitrile were dissolved 0.44 g of ethyl 7-(3,5-di-tert.-butyl-4-hydroxybenzylideneamino)cephalosporanate and 0.10 g of 5-mercapto-1-methyl-1H-tetrazole. To the resulting solution was added 1.0 g of a solution of boron trifluoride in acetonitrile (0.1718 g/g) with ice-cooling, and the resulting mixture was stirred at room temperature for four hours. After the completion of the reaction, the solvent was removed by distillation under reduced pressure, and to the resulting residue were added 10 ml of ethyl acetate and a solution of 0.13 g of p-toluenesulfonic acid monohydrate in 5 ml of water to dissolve the residue, after which the resulting solution was stirred for 30 minutes with ice-cooling. The aqueous layer was separated, and 5 ml of ethyl acetate was added to the aqueous layer, after which the pH of the solution was adjusted to 7.0 by adding sodium hydrogen carbonate to the solution. The organic layer was thereafter separated, washed with water and saturated aqueous sodium chloride solution in this order, and then dried on magnesium sulfate, after which a solution of 0.1 g of p-toluenesulfonic acid monohydrate in 2 ml of ethyl acetate was added to the dried organic layer. The solvent was removed by distillation under reduced pressure and diethyl ether was added to the resulting residue, after which the resulting mixture was subjected to filtration to obtain 0.35 g (yield 77.8%) of finely divided p-toluenesulfonic acid salt of ethyl 7-amino-3-[5-(1-methyl-1,2,3,4-tetrazolyl)thiomethyl]-$\Delta^3$-cephem-4-carboxylate having a melting point of 115°–122° C. decomp.).

EXAMPLE 29

In 3 ml of acetonitrile were dissolved 0.65 g of diphenylmethyl 7-(3,5-di-tert.-butyl-4-hydroxybenzylideneamino)cephalosporanate and 0.12 g of 5-mercapto-1-methyl-1H-tetrazole, and 1.2 g of a solution of boron trifluoride in acetonitrile (0.1718 g/g) was added to the resulting solution. The resulting mixture was stirred at 30° C. for 30 minutes, and the solvent was thereafter removed by distillation under reduced pressure. To the residue thus obtained were added 5 ml of water and 10 ml of ethyl acetate to dissolve the residue. The aqueous layer was thereafter separated and then washed with 5 ml of ethyl acetate. To this aqueous solution was added 5 ml of acetone, and the pH of the solution was then adjusted to 4.0 by adding concentrated ammonia water with icecooling. The crystals thus precipitated were collected by filtration, washed with 2 ml of water and then 5 ml of acetone, and thereafter dried to obtain 0.25 g (yield 76.7%) of 7-amino-3-[5-(1-methyl-1,2,3,4-tetrazolyl)thiomethyl]-$\Delta^3$-cephem-4-carboxylic acid.

EXAMPLE 30

When in the same manner as in Example 29, a suitable thiol compound represented by the general formula (III) is used in place of the 5-mercapto-1-methyl-1H-tetrazole the following objective compounds are obtained in a yield of 75 to 90% or more:

7-amino-3-[2-(5-methyl-1,3,4-thiadiazolyl)thiomethyl]-$\Delta^3$-cephem-4-carboxylic acid, 7-amino-3-[2-(1,3,4-thiadiazolyl)thiomethyl]-$\Delta^3$-cephem-4-carboxylic acid, 7-amino-3-[5-(1-ethyl-1,2,3,4-tetrazolyl)thiomethyl]-$\Delta^3$-cephem-4-carboxylic acid, 7-amino-3-[5-(1-phenyl-1,2,3,4-tetrazolyl)thiomethyl]-$\Delta^3$-cephem-4-carboxylic acid, 7-amino-3-[5-(1-carboxylmethyl-1,2,3,4-tetrazolyl)thiomethyl]-$\Delta^3$-cephem-4-carboxylic acid, 7-amino-3-[5-(1-methoxycarbonylmethyl-1,2,3,4-tetrazolyl)thiomethyl]-$\Delta^3$-cephem-4-carboxylic acid, 7-amino-3-[5-(1-carbamoylmethyl-1,2,3,4-tetrazolyl)thiomethyl]-$\Delta^3$-cephem-4-carboxylic acid, 7-amino-3-[5-(1,2,3,4-tetrazolyl)thiomethyl]-$\Delta^3$-cephem-4-carboxylic acid, 7-amino-3-(carboxymethylthiomethyl)-$\Delta^3$-cephem-4-carboxylic acid, p0 7-amino-3-(ethoxycarbonylmethylthiomethyl)-$\Delta^3$-cephem-4-carboxylic acid, 7-amino-3-(propylthiomethyl)-$\Delta^3$-cephem-4-carboxylic acid, 7-amino-3-(phenylthiomethyl)-$\Delta^3$-cephem-4-carboxylic acid, and 7-amino-3-[5-(1,2,3-triazolyl)thiomethyl]-$\Delta^3$-cephem-4-carboxylic acid.

What is claimed is:

1. A process for producing a 7-(substituted)amino-3-substituted thiomethyl cephem carboxylic acid represented by the formula:

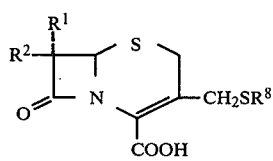

(I)

wherein $R^1$ is a hydrogen atom or $C_{1-4}$ alkyloxy group; $R^2$ is an amino group or a protected amino group represented by the formula

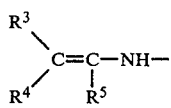

in which $R^3$, $R^4$ and $R^5$, which may be identical or different, are hydrogen atoms or conventional cephalosporin substituents which do not participate in the reaction, or the formula

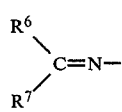

in which $R^6$ and $R^7$, which may be identical or different, are hydrogen atoms or conventional cephalosporin substituents which do not participate in the reaction; and $R^8$ is a moiety of a compound of the formula $HSR^8$ wherein $SR^8$ is a conventional 3-position cephalosporin thio substituent, or said compound (I) in which the carboxyl group is protected by a conventional cephalosporin carboxy protecting group or a conventional cephalosporin salt thereof, which comprises reacting a cephalosporanic acid represented by the formula:

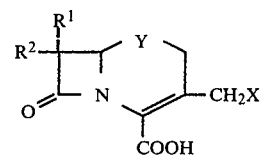

(II)

wherein $R^1$ and $R^2$ have the same meanings as defined above; X is carboxylic acyloxy or carbamoyloxy groups or one of said groups substituted by a conventional cephalosporin substituent; $>Y$ is $>S$ or $>S\rightarrow O$; or said compound (II) in which the carboxyl group is protected by a conventional cephalosporin carboxy protective group or a conventional cephalosporin salt thereof with a thiol compound represented by the formula, $$R^8-SH \qquad (III)$$

wherein $R^8$ has the same meaning as defined above, or a salt thereof with a compound forming a conventional cephalosporin salt, in a non-aqueous organic solvent at a temperature of $-20°$ to $80°$ C. in the presence of boron trifluoride or a complex compound thereof which acts as boron trifluoride, the boron and the fluorine bonded to boron in said complex compound being present as $BF_3$.

2. The process according to claim 1, wherein $R^2$ is an amino group.

3. The process according to claim 1, wherein $R^2$ is a group represented by the formula

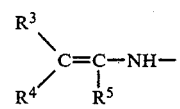

in which $R^3$, $R^4$ and $R^5$ have the same meaning as defined in claim 1.

4. The process according to claim 1, wherein $R^2$ is a group represented by the formula

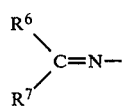

in which $R^6$ and $R^7$ have the same meanings as defined in claim 1.

5. The process according to claim 1, wherein the starting compound is a salt of the compound represented by the formula (II).

6. The process according to claim 5, wherein the salt of the compound represented by the formula (II) is a salt at an acidic group of the compound II.

7. The process according to claim 5, wherein the salt of the compound represented by the formula (II) is a salt at a basic group of the compound (II).

8. The process according to claim 6, wherein the salt is an alkali metal salt.

9. The process according to claim 8, wherein the alkali metal is sodium.

10. The process according to claim 7, wherein the salt is a mineral acid salt or a sulfonic acid salt.

11. The process according to claim 10, wherein the mineral acid salt is a hydrochloric acid salt.

12. The process according to claim 10, wherein the sulfonic acid salt is a p-toluenesulfonic acid salt.

13. The process according to claim 1, wherein the starting compound is an ester of the compound represented by the formula (II).

14. The process according to claim 1, wherein $>Y$ is $>S$.

15. The process according to claim 1, wherein $>Y$ is $>S \rightarrow O$.

16. The process according to claim 1, wherein $R^1$ is a hydrogen atom.

17. The process according to claim 1, wherein $R^1$ is a $C_{1-4}$ alkyloxy group.

18. The process according to claim 17, wherein $R^1$ is a methoxy group.

19. The process according to claim 1, wherein X is a $C_{1-8}$ acyloxy group.

20. The process according to claim 19, wherein X is a $C_{1-8}$ alkanoyloxy group.

21. The process according to claim 20, wherein X is acetoxy.

22. The process according to claim 3, wherein $R^3$, $R^4$ and $R^5$, which may be identical or different, are unsubstituted or substituted $C_{1-5}$ alkyl, $C_{2-4}$ alkenyl, $C_{5-7}$ cycloalkyl, $C_{5-7}$ cycloalkenyl, aryl, aralkyl, ring carbon containing heterocyclic containing O, N and S atoms alone or in any combination in any position of the ring, or carboxylic acyl.

23. The process according to claim 4, wherein $R^6$ and $R^7$, which may be identical or different, are hydrogen, unsubstituted or substituted $C_{1-5}$ alkyl, $C_{2-4}$ alkenyl, $C_{5-7}$ cycloalkyl, $C_{5-7}$ cycloalkenyl, aryl, aralkyl, ring carbon containing heterocyclic containing O, N and S atoms alone or in any combination in any position of the ring, or carboxylic acyl hydrocarbon.

24. The process according to claim 23, wherein $R^6$ and $R^7$ are different from each other and represent hydrogen or unsubstituted or substituted aryl hydrocarbon.

25. The process according to claim 24, wherein $R^6$ is hydrogen, and $R^7$ is 2-hydroxyphenyl or 3,5-di-tert.-butyl-4-hydroxyphenyl.

26. The process according to claim 1, wherein the organic solvent is a nitrile, a nitroalkane, an organic carboxylic acid, a ketone, an ether or a sulfolane.

27. The process according to claim 1, wherein the reaction is effeced in the presence of a dehydrating agent to maintain anhydrous conditions.

28. The process according to claim 1, wherein the reaction is effected in the presence of boron trifluoride.

29. The process according to claim 1, wherein the reaction is effected in the presence of a boron trifluoride complex compound.

30. The process according to claim 29, wherein the boron trifluoride complex compound is a dialkyl ether complex, an amine complex, an aliphatic acid complex, a nitrile complex, a carboxylic ester complex, or a phenol complex.

31. The process according to claim 30, wherein the boron trifluoride complex compound is a dialkyl ether complex, an aliphatic acid complex, or a nitrile complex.

32. The process according to claim 1, wherein $R^8$ is an unsubstituted or substituted alkyl, cycloalkyl, aryl hydrocarbon, aralkyl, carboxylic acyl, thiocarbamoyl, alkoxythiocarbonyl, aryloxythiocarbonyl, cycloalkyloxythiocarbonyl, amidino or ring carbon containing heterocyclic group.

33. The process according to claim 32, wherein $R^8$ is an unsubstituted or substituted $C_{1-8}$ alkyl, aryl or nitrogen-containing ring carbon containing heterocyclic group, said heterocyclic group containing at least one nitrogen atom with or without oxygen or sulfur.

34. The process according to claim 33, wherein $R^8$ is an unsubstituted or substituted $C_{1-8}$ alkyl group.

35. The process according to claim 33, wherein $R^8$ is an unsubstituted or substituted nitrogen-containing ring carbon containing heterocyclic group which contains at least one nitrogen atom with or without oxygen or sulfur.

36. The process according to claim 35, wherein $R^8$ is an unsubstituted or substituted tetrazolyl, thiadiazolyl, triazolyl, oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, oxadiazolyl, thiadiazolyl, thiatriazolyl, triazinyl, benzimidazolyl, benzoxazolyl, benzothiazolyl, triazolopyridyl, purinyl, pyridine-1-oxide-2-yl, pyridazine-1-xide-6-yl, tetrazolopyridazinyl, tetrazolopyrimidinyl, thiazolopyridazinyl, thiadiazolopyridazinyl or triazolopyrimidinyl.

37. The process according to claim 36, wherein $R^8$ is an unsubstituted or substituted tetrazolyl, thiadiazolyl, or triazolyl.

38. The process according to claim 37, wherein $R^8$ is 2-(5-methyl-1,3,4-thiadiazolyl), 2-(1,3,4-thiadiazolyl), 2-(1-methyl-1,3,4-triazolyl), 5-(1,2,3,4-tetrazolyl), 5-(1-methyl-1,2,3,4-tetrazolyl), 5-(1-carbamoylmethyl-1,2,3,4-tetrazolyl), 5-[1-(2-hydroxyethyl)-1,2,3,4-tetrazolyl], 5-(1-vinyl-1,2,3,4-tetrazolyl), 5-[1-(2-aminoethyl)-1,2,3,4-tetrazolyl], 5-[2-(2-N,N-dimethylaminoethyl)-1,2,3,4-tetrazolyl]or 5-[1-(2-N,N-dimethylaminoethyl)-1,2,3,4-tetrazolyl].

39. The process according to claim 2, wherein $R^1$ is a hydrogen atom and $R^8$ is an unsubstituted or substituted alkyl, aryl hydrocarbon or ring carbon containing heterocyclic group.

40. The process according to claim 39, wherein $R^8$ is an unsubstituted or substituted nitrogen-containing heterocyclic group which contains at least one nitrogen atom with or without oxygen or sulfur.

41. The process according to claim 40, wherein $R^8$ is unsubstituted or substituted tetrazolyl, thiadiazolyl, triazolyl, oxazolyl, thiazolyl, isoxazolyl, isothiazolyl, imidazolyl, pyrazolyl, pyridyl, pyrazinyl, pyrimidinyl, pyridazinyl, quinolyl, isoquinolyl, quinazolyl, indolyl, indazolyl, oxadiazolyl, thiadiazolyl, thiatriazolyl, triazinyl, benzimidazolyl, benzoxazolyl, benzothiazolyl, triazolopyridyl, purinyl, pyridine-1-oxide-2-yl, pyridazine-1-oxide-6-yl, tetrazolopyridazinyl, tetrazolopyrimidinyl, thiazolopyridazinyl, thiadiazolopyridazinyl or triazolopyrimidinyl.

42. The process according to claim 39, wherein $R^8$ is n-propyl, carboxymethyl, ethoxycarbonylmethyl, phenyl, 5-(1,2,3,4-tetrazolyl), 5-(1-methyl-1,2,3,4-tetrazolyl), 5-(1-ethyl-1,2,3,4-tetrazolyl), 5-(1-sulfomethyl-1,2,3,4-tetrazolyl), 5-(1-carboxymethyl-1,2,3,4-tetrazolyl), 5-[2-(2-carbamoyletyl)-1,2,3,4-tetrazolyl], 5-[1-(2-sulfamoylethyl)-1,2,3,4-tetrazolyl], 5-[1-(2-N,N-dimethylaminoethyl)-1,2,3,4-tetrazolyl], 5-[2-(2-N,N-dimethylaminoethyl)-1,2,3,4-tetrazolyl], 5-[1-(2-N,N-diethylaminoethyl)-1,2,3,4-tetrazolyl], 5-(1-methoxycarbonylmethyl-1,2,3,4-tetrazolyl), 5-(1-carbamoylmethyl-1,2,3,4-tetrazolyl), 5-[1-(2-hydroxyethyl)-1,2,3,4-tetrazolyl], 5-[1-(2-aminoethyl)-1,2,3,4-tetrazolyl], 5-(1-phenyl-1,2,3,4-tetrazolyl), 5-(1-vinyl-1,2,3,4-tetrazolyl), 2-(1,3,4-thiadiazolyl), 2-(5-methyl-1,3,4-thiadiazolyl), 2-(5-ethyl-1,3,4-thiadiazolyl), 2-(5-amino-1,3,4-thiadiazolyl), 2-(5-phenyl-1,3,4-thiadiazolyl), 5-(3-methyl-1,2,4-thiadiazolyl), 2-(5-carboxymethyl-1,3,4-thiadiazolyl), 5-(1,2,3-triazolyl), 2-(1-methyl-1,3,4-triazolyl), 2-(5-methyl-1,3,4-triazolyl), 2-(1,5-dimethyl-1,3,4-triazolyl), 4-(5-ethoxycarbonyl-1,2,3-triazolyl), 4-(5-carboxyl-1,2,3-triazolyl), 2-(5-ethoxycarbonylmethyl-1,3,4-triazolyl), benzoxazolyl, 2-(benzimidazolyl), 2-(5-methyl-1,3,4-oxadiazolyl), 2-(5-methyl-1,3-thiazolyl), 2-(5-methyl-1,3-oxazolyl), 2-(1,3-thiazolyl), 5-(1,2,3,4-thiatriazolyl) or 2-(imidazolyl).

43. The process according to claim 42, wherein $R^8$ is 2-(1,3,4-thiadiazolyl), 2-(5-methyl-1,3,4-thiadiazolyl), 2-(1-methyl-1,3,4-triazolyl), 5-(1,2,3,4-tetrazolyl), 5-(1-methyl-1,2,3,4-tetrazolyl), 5-(1-carbamoylmethyl-1,2,3,4-tetrazolyl), 5-[1-(2-hydroxyethyl)-1,2,3,4-tetrazolyl], 5-(1-vinyl-1,2,3,4-tetrazolyl), 5-[1-(2-aminoethyl)-1,2,3,4-tetrazolyl], 5-[2-(2-N,N-dimethylaminoethyl)-1,2,3,4-tetrazolyl], or 5-[1-(2-N,N-dimethylaminoethyl)-1,2,3,4-tetrazolyl].

44. The process according to claim 42, wherein the objective compound is a compound represented by the formula (I) set forth in claim 1.

45. The process according to claim 42, wherein a compound represented by the formula (II) set forth in claim 1 wherein >Y is >S and X is acetoxy is used as the starting compound.

46. The process according to claim 1, wherein $R^1$ is a hydrogen atom, $R^2$ is 2-hydroxybenzylideneamino and $R^8$ is an unsubstituted or substituted alkyl, aryl hydrocarbon or ring carbon containing heterocyclic group.

47. The process according to claim 46, wherein $R^8$ is n-propyl, carboxymethyl, ethoxycarbonylmethyl, phenyl, 5-(1,2,3,4-tetrazolyl), 5-(1-methyl-1,2,3,4-tetrazolyl), 5-(1-ethyl-1,2,3,4-tetrazolyl), 5-(1-sulfomethyl-1,2,3,4-tetrazolyl), 5-(1-carboxymethyl-1,2,3,4-tetrazolyl), 5-[2-(2-carbamoylethyl)-1,2,3,4-tetrazolyl], 5-[1-(2-sulfamoylethyl)-1,2,3,4-tetrazolyl], 5-[1-(2-N,N-dimethylaminoethyl)-1,2,3,4-tetrazolyl], 5-[2-(2-N,N-dimethylaminoethyl)-1,2,3,4-tetrazolyl], 5-[1-(2-N,N-diethylaminoethyl)-1,2,3,4-tetrazolyl], 5-(1-methoxycarbonylmethyl-1,2,3,4-tetrazolyl), 5-(1-carbamoylmethyl-1,2,3,4-tetrazolyl), 5-[1-(2-hydroxyethyl)-1,2,3,4-tetrazolyl], 5-[1-(2-aminoethyl)-1,2,3,4-tetrazolyl], 5-(1-phenyl-1,2,3,4-tetrazolyl), 5-(1-vinyl-1,2,3,4-tetrazolyl), 2-(1,3,4-thiadiazolyl), 2-(5-methyl-1,3,4-thiadiazolyl), 2-(5-ethyl-1,3,4-thiadiazolyl), 2-(5-amino-1,3,4-thiadiazolyl), 2-(5-phenyl-1,3,4-thiadiazolyl), 5-(3-methyl-1,2,4-thiadiazolyl), 2-(5-carboxymethyl-1,3,4-thiadiazolyl, 5-(1,2,3-triazolyl), 2-(1-methyl-1,3,4-triazolyl), 2-(5-methyl-1,3,4-triazolyl), 2-(1,5-dimethyl-1,3,4-triazolyl), 4-(5-ethoxycarbonyl-1,2,3-triazolyl), 4-(5-carboxyl-1,2,3-triazolyl), 2-(5-ethoxycarbonylmethyl-1,3,4-triazolyl), benzoxazolyl, 2-(benzimidazolyl), 2-(5-methyl-1,3,4-oxadiazolyl), 2-(5-methyl-1,3-thiazolyl), 2-(5-methyl-1,3-oxazolyl), 2-(1,3-thiazolyl), 5-(1,2,3,4-thiatriazolyl) or 2-(imidazolyl).

48. The process according to claim 47, wherein $R^8$ is 2-(1,3,4-thiadiazolyl), 2-(5-methyl-1,3,4-thiadiazolyl), 2-(1-methyl-1,3,4-triazolyl), 5-(1,2,3,4-tetrazolyl), 5-(1-methyl-1,2,3,4-tetrazolyl), 5-(1-carbamoylmethyl-1,2,3,4-tetrazolyl), 5-[1-(2-hydroxyethyl)-1,2,3,4-tetrazolyl], 5-(1-vinyl-1,2,3,4-tetrazolyl), 5-[1-(2-aminoethyl)-1,2,3,4-tetrazolyl], 5-[2-(2-N,N-dimethylaminoethyl)-1,2,3,4-tetrazolyl], or 5-[1-(2-N,N-dimethylaminoethyl)-1,2,3,4-tetrazolyl].

49. The process according to claim 48, wherein the objective compound is a compound represented by the formula (I) set forth in claim 1.

50. The process according to claim 49, wherein a compound represented by the formula (II) set forth in claim 1 wherein >Y is >S and X is acetoxy is used as the starting compound.

51. The process according to claim 1, wherein $R^1$ is a hydrogen atom, $R^2$ is a 3, 5-di-tert.-butyl-4-hydroxybenzylideneamino group and $R^8$ is unsubstituted or substituted alkyl, aryl hydrocarbon or ring carbon containing heterocyclic group.

52. The process according to claim 51, wherein $R^8$ is n-propyl, carboxymethyl, ethoxycarbonylmethyl, phenyl, 5-(1,2,3,4-tetrazolyl), 5-(1-methyl-1,2,3,4-tetrazolyl), 5-(1-ethyl-1,2,3,4-tetrazolyl), 5-(1-sulfomethyl-1,2,3,4-tetrazolyl), 5-(1-carboxymethyl-1,2,3,4-tetrazolyl), 5-[2-(2-carbamoylethyl)-1,2,3,4-tetrazolyl], 5-[1-(2-sulfamoylethyl)-1,2,3,4-tetrazolyl], 5-[1-(2-N,N-dimethylaminoethyl)-1,2,3,4-tetrazolyl], 5-[2-(2-N,N-dimethylaminoethyl)-1,2,3,4-tetrazolyl], 5-[1-(2-N,N-diethylaminoethyl)-1,2,3,4-tetrazolyl], 5-(1-methoxycarbonylmethyl-1,2,3,4-tetrazolyl), 5-(1-carbamoylmethyl-1,2,3,4-tetrazolyl), 5-[1-(2-aminoethyl)-1,2,3,4-tetrazolyl], 5-[1-(2-hydroxyethyl)-1,2,3,4-tetrazolyl], 5-(1-phenyl-1,2,3,4-tetrazolyl), 5-(1-vinyl-1,2,3,4-tetrazolyl), 2-(1,3,4-thiadiazolyl), 2-(5-methyl-1,3,4-thiadiazolyl), 2-(5-ethyl-1,3,4-thiadiazolyl), 2-(5-amino-1,3,4-thiadiazolyl), 2-(5-phenyl-1,3,4-thiadiazolyl), 5-(3-methyl-1,2,4-thiadiazolyl), 2-(5-carboxymethyl-1,3,4-thiadiazolyl), 5-(1,2,3-triazolyl), 2-(1-methyl-1,3,4-triazolyl), 2-(5-methyl-1,3,4-triazolyl), 2-(1,5-dimethyl-1,3,4-triazolyl), 4-(5-ethoxycarbonyl-1,2,3-triazolyl), 4-(5-carboxyl-1,2,3-triazolyl), 2-(5-ethoxycarbonylmethyl-1,3,4-triazolyl), benzoxazolyl, 2-(benzimidazolyl), 2-(5-methyl-1,3,4-oxadiazolyl), 2-(5-methyl-1,3-thiazolyl), 2-(5-methyl-1,3-oxazolyl), 2-(1,3-thiazolyl), 5-(1,2,3,4-thiatriazolyl) or 2-(imidazolyl).

53. The process according to claim 52, wherein $R^8$ is 2-(1,3,4-thiadiazolyl), 2-(5-methyl-1,3,4-thiadiazolyl), 2-(1-methyl-1,3,4-triazolyl), 5-(1,2,3,4-tetrazolyl), 5-(1-methyl-1,2,3,4-tetrazolyl), 5-(1-carbamoylmethyl-1,2,3,4-tetrazolyl), 5-[1-(2-hydroxyethyl)-1,2,3,4-tetrazolyl], 5-(1-vinyl-1,2,3,4-tetrazolyl), 5-[1-(2-aminoethyl)-1,2,3,4-tetrazolyl], 5-[2-(2-N,N-dimethylaminoethyl)-1,2,3,4-tetrazolyl] or 5-[1-(2-N,N-dimethylaminoethyl)-1,2,3,4-tetrazolyl].

54. The process according to claim 53, wherein the objective compound is a compound represented by the formula (I) set forth in claim 1.

55. The process according to claim 54, wherein a compound represented by the formula (II) set forth in claim 1 wherein >Y is >S and X is acetoxy is used as the starting compound.

56. The process according to claim 2, wherein $R^1$ is a $C_{1-4}$ alkyloxy group and $R^8$ is an unsubstituted or substituted ring carbon containing heterocyclic group.

57. The process according to claim 56, wherein $R^1$ is a methoxy group and $R^8$ is 5-(1,2,3,4-tetrazolyl), 5-(1-methyl-1,2,3,4-tetrazolyl), 5-(1-ethyl-1,2,3,4-tetrazolyl), 5-(1-sulfomethyl-1,2,3,4-tetrazolyl), 5-(1-carboxymethyl-1,2,3,4-tetrazolyl), 5-[2-(2-carbamoylethyl)-1,2,3,4-tetrazolyl], 5-[1-(2-sulfamoylethyl)-1,2,3,4-tetrazolyl], 5-[1-(2-N,N-dimethylaminoethyl)-1,2,3,4-tetrazolyl], 5-[2-(2-N,N-dimethylaminoethyl)-1,2,3,4-tetrazolyl], 5-[2-(2-N,N-diethylaminoethyl)-1,2,3,4-tetrazolyl], 5-(1- methoxycarbonylmethyl-1,2,3,4-tetrazolyl), 5-(1-carbamoylmethyl-1,2,3,4-tetrazolyl), 5-[1-(2-hydroxyethyl)-1,2,3,4-tetrazolyl], 5-[1-(2-aminoethyl)-1,2,3,4-tetrazolyl], 5-(1-phenyl-1,2,3,4-tetrazolyl), 5-(1-vinyl-1,2,3,4-tetrazolyl), 2-(1,3,4-thiadiazolyl), 2-(5-methyl-1,3,4-thiadiazolyl), 2-(5-ethyl-1,3,4-thiadiazolyl), 2-(5-amino-1,3,4-thiadiazolyl), 2-(5-phenyl-1,3,4-thiadiazolyl), 5-(3-methyl-1,2,4-thiadiazolyl), 2-(5-carboxymethyl-1,3,4-thiadiazolyl), 5-(1,2,3-triazolyl), 2-(1-methyl-1,3,4-triazolyl), 2-(5-methyl-1,3,4-triazolyl), 2-(1,5-dimethyl-1,3,4-triazolyl), 4-(5-ethoxycarbonyl-1,2,3-triazolyl), 4-(5-carboxyl-1,2,3-triazolyl), 2-(5-ethoxycarbonylmethyl-1,3,4-triazolyl), benzoxazolyl, 2-(benzimidazolyl), 2-(5-methyl-1,3,4-oxadiazolyl), 2-(5-methyl-1,3-thiazolyl), 2-(5-methyl-1,3-oxazolyl), 2-(1,3-thiazolyl), 5-(1,2,3,4-thiatriazolyl) or 2-(imidazolyl).

58. The process according to claim 57, wherein $R^8$ is 2-(1,3,4-thiadiazolyl), 2-(5-methyl-1,3,4-thiadiazolyl), 2-(1-methyl-1,3,4-triazolyl), 5-(1,2,3,4-tetrazolyl), 5-(1-methyl-1,2,3,4-tetrazolyl), 5-(1-carbamoylmethyl-1,2,3,4-tetrazolyl), 5-[1-(2-hydroxyethyl)-1,2,3,4-tetrazolyl], 5-(1-vinyl-1,2,3,4-tetrazolyl), 5-[1-(2-aminoethyl)-1,2,3,4-tetrazolyl], 5-[2-(2-N,N-dimethylaminoethyl)-1,2,3,4-tetrazolyl] or 5-[1-(2-N,N-dimethylaminoethyl)-1,2,3,4-tetrazolyl].

59. The process according to claim 58, wherein the objective compound is a compound represented by the formula (I) set forth in claim 1.

60. The process according to claim 59, wherein a compound represented by the formula (II) set forth in claim 1 wherein $>Y$ is $>S$ and X is acetoxy is used as the starting compound.

61. The process according to claim 2, wherein $R^1$ is a hydrogen atom, $>Y$ is $>S\rightarrow O$ and X is acetoxy.

62. The process according to claim 2, wherein $R^1$ is a hydrogen atom, $>Y$ is $>S$ and X is acetoxy.

63. The process according to claim 45, wherein a salt of the compound represented by the formula (II) set forth in claim 1 is used as the starting compound.

64. The process according to claim 42, wherein the objective compound is an ester of the compound represented by the formula (I) set forth in claim 1.

65. The process according to claim 42, wherein the objective compound is a salt of the compound represented by the formula (I) set forth in claim 1.

66. The process according to claim 44, wherein a compound represented by the formula (II) set forth in claim 1 wherein $>Y$ is $>S$, and X is carboxylic acyloxy having 1 to 8 carbon atoms is used as the starting compound.

67. The process according to claim 45, wherein the organic solvent is a nitrile, ether, nitroalkane, organic carboxylic acid or sulfolane.

68. The process according to claim 45, wherein the reaction is effected in the presence of a dehydrating agent.

69. The process according to claim 45, wherein the reaction is effected in the presence of boron trilfuoride.

70. The process according to claim 45, wherein the boron trifluoride complex compound is a dialkyl ether complex, an amine complex, an aliphatic acid complex, a nitrile complex, a carboxylic ester complex or a phenol complex.

71. The process according to claim 45, wherein the boron trifluoride complex compound is a dialkyl ether complex, an aliphatic acid complex or a nitrile complex.

72. The process according to claim 67, wherein the reaction is effected in the presence of boron trifluoride.

73. The process according to claim 72, wherein the reaction is effected in the presence of a dehydrating agent.

74. The process according to claim 72, wherein a salt of the compound represented by the formula (II) set forth in claim 1 is used as the starting compound.

75. The process according to claim 72, wherein the objective compound is an ester of the compound represented by the formula (I) set forth in claim 1.

76. The process according to claim 72, wherein the objective compound is a salt of the compound represented by the formula (I) set forth in claim 1.

77. The process according to claim 1, wherein the organic solvent is in the form of a complex with boron trifluoride.

78. The process according to claim 45, wherein $R^8$ is 5-(1-methyl-1,2,3,4-tetrazolyl).

79. The process according to claim 50, wherein $R^8$ is 5-(1-methyl-1,2,3,4-tetrazolyl).

80. The process according to claim 55, wherein $R^8$ is 5-(1-methyl-1,2,3,4-tetrazolyl).

81. The process according to claim 65, wherein $R^8$ is 5-(1-methyl-1,2,3,4-tetrazolyl).

82. The process according to claim 45, wherein $R^8$ is 2-(5-methyl-1,3,4-thiadiazolyl).

83. The process according to claim 72, wherein the boron trifluoride or boron trifluoride complex compound is used in an amount of 2 to 7 moles per mole of the compound represented by the formula (II) set forth in claim 1.

84. The process according to claim 72, wherein the amount of the thiol compound represented by the general formula (III) is 1 to 1.5 moles per mole of the compound represented by the formula (II).

85. The process according to claim 45, wherein the organic solvent is a complex of a nitrile, an ether or an aliphatic acid with a boron trifluoride.

86. The process according to claim 82, wherein the organic solvent is a complex of a nitrile, an ether or an aliphatic acid with a boron trifluoride.

87. The process according to claim 36, wherein $R^8$ is a 5-(1,2,3,4-tetrazolyl), 5-(1-methyl-1,2,3,4-tetrazolyl), 5-(1-ethyl-1,2,3,4-tetrazolyl), 5-(1-sulfomethyl-1,2,3,4-tetrazolyl), 5-(1-carboxylmethyl-1,2,3,4-tetrazolyl), 5-[2-(2-carbamoylethyl)-1,2,3,4-tetrazolyl], 5-[1-(2-sulfamoylethyl)-1,2,3,4-tetrazolyl], 5-[1-(2-N,N-dimethylaminoethyl)-1,2,3,4-tetrazolyl], 5-[2-(2-N,N-dimethylaminoethyl)-1,2,3,4-tetrazolyl], 5-[1-(2-N,N-diethylaminoethyl)-1,2,3,4-tetrazolyl], 5-(1-methoxycarbonylmethyl-1,2,3,4-tetrazolyl), 5-(1-carbamoylmethyl-1,2,3,4-tetrazolyl), 5-[1-(2-aminoethyl)-1,2,3,4-tetrazolyl], 5-[1-(2-hydroxyethyl)-1,2,3,4-tetrazolyl], 5-(1-phenyl-1,2,3,4-tetrazolyl), 5-(1-vinyl-1,2,3,4-tetrazolyl), 2-(1,3,4-thiadiazolyl), 2-(5-methyl-1,3,4-thiadiazolyl), 2-(5-ethyl-1,3,4-thiadiazolyl), 2-(5-amino-1,3,4-thiadiazolyl), 2-(5-phenyl-1,3,4-thiadiazolyl), 5-(3-methyl-1,2,4-thiadiazolyl), 2-(5-carboxymethyl-1,3,4-thiadiazolyl), 5-(1,2,3-triazolyl), 2-(1-methyl-1,3,4-triazolyl), 2-(5-methyl-1,3,4-triazolyl), 2-(1,5-dimethyl-1,3,4-triazolyl), 4-(5-ethoxycarbonyl-1,2,3-triazolyl), 4-(5-carboxyl-1,2,3-triazolyl), 2-(5-ethoxycarbonyl-1,3,4-triazolyl), benzoxazolyl, 2-(benzimidazolyl), 2-(5-methyl-1,3,4-oxadiazolyl), 2-(5-methyl-1,3-thiazolyl), 2-(5-methyl-1,3-oxazolyl), 2-(1,3-thiazolyl), 5-(1,2,3,4-thiatriazolyl) or 2-(imidazolyl).

88. The process of claim 1 wherein the complex compound of boron trifluoride is a coordination compound of boron trifluoride.

* * * * *